(12) United States Patent
Chou et al.

(10) Patent No.: US 7,985,567 B2
(45) Date of Patent: Jul. 26, 2011

(54) HOST CELLS AND METHODS FOR PRODUCING 3-METHYL-2-BUTEN-1-OL, 3-METHYL-3-BUTEN-1-OL, AND 3-METHYL-BUTAN-1-OL

(75) Inventors: Howard H. Chou, Berkeley, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/646,189

(22) Filed: Dec. 23, 2009

(65) Prior Publication Data

US 2010/0205855 A1    Aug. 19, 2010

Related U.S. Application Data

(60) Provisional application No. 60/947,285, filed on Jun. 29, 2007.

(51) Int. Cl.
*C12P 7/02* (2006.01)
*C12N 1/20* (2006.01)
*C12N 1/00* (2006.01)
*C12N 1/12* (2006.01)
*C12N 5/00* (2006.01)

(52) U.S. Cl. .......... 435/155; 435/157; 435/252.3; 435/252.33; 435/254.11; 435/254.21; 435/257.2; 435/325

(58) Field of Classification Search .......... None
See application file for complete search history.

(56) References Cited

U.S. PATENT DOCUMENTS

| | | | |
|---|---|---|---|
| 4,609,624 | A | 9/1986 | Rothlisberger |
| 5,460,949 | A | 10/1995 | Saunders et al. |
| 6,190,895 | B1 | 2/2001 | Croteau et al. |
| 6,291,745 | B1 | 9/2001 | Meyer et al. |
| 6,515,202 | B1 | 2/2003 | Crane et al. |
| 6,531,303 | B1 | 3/2003 | Millis et al. |
| 6,689,593 | B2 | 2/2004 | Millis et al. |
| 2003/0148479 | A1 | 8/2003 | Keasling et al. |
| 2003/0219798 | A1 | 11/2003 | Gokarn et al. |
| 2004/0005678 | A1 | 1/2004 | Keasling et al. |
| 2004/0029239 | A1 | 2/2004 | Ohto et al. |
| 2004/0063182 | A1 | 4/2004 | Ohto et al. |
| 2004/0077039 | A1 | 4/2004 | Holtzman et al. |
| 2004/0110259 | A1 | 6/2004 | Baugh et al. |
| 2004/0194162 | A1 | 9/2004 | Hahn et al. |
| 2007/0087425 | A1 | 4/2007 | Ohto |

OTHER PUBLICATIONS

Chang et al, Production of isoprenoid pharmaceuticals by engineered microbes, Nature Chem Biology, (online) Nov. 15, 2006, pp. 1-8.
Keasling et al, 5-Carbon Alcohols for Drop-in Gasoline Replacement, LBNL Technology Announcement, posted online Sep. 2, 2009.
Martin et al, Engineering a mevalonate pathway in *Escherichia coli* for production of terpenoids, Nature Biotechnology (Jul. 2003), vol. 21, No. 7, pp. 796-802.
Maury et al, Microbial Isoprenoid Production: An Example of Green Chemistry through Metabolic Engineering, Adv Biochem Engin/Biotechnol (2005) 10: 19-51.
Rigden et al, A cofactor-dependent phosphoglycerate mutase homolog from *Bacillus stearothermophilus* is actually a broad specificity phosphatase. Protein Science 2001, 10:1835-1846; p. 1841, col. 2; p. 1842.
Smolenskii et al, a Study of the Structure-Octane Number Relationship for Hydrocarbons, Doklady Physical Chemistry, vol. 397, Part 1, 2004, pp. 145-149. Translated from Doklady Akademii Nauk, vol. 397, No. 2, 2004, pp. 219-224.
Withers et al, Identification of Isopentenol Biosynthetic Genes from *Bacillus subtilis* by a Screening Method Based on Isoprenoid Precursor Toxicity, Applied and Environmental Microbiology, Oct. 2007, pp. 6277-6283.
Polakowski et al, Overexpression of a cytosolic hydroxymethylglutaryl-CoA reductase leads to squalene accumulation in yeast, Appl Microbiol Biotechnol (1998) 49: 66-71.
Wilding et al, Identification, Evolution, and Essentiality of the Mevalonate Pathway for Isopentenyl Diphosphate Biosynthesis in Gram-Positive Cocci. J.Bacteriology, Aug. 2000, vol. 182, No. 15, pp. 4319-4327.
Donald et al, Effects of Overproduction of the Catalytic Domain of 3-Hydroxy-3-Methylglutaryl Coenzyme A Reductase on Squalene Synthesis in *Saccharomyces cerevisiae*. Appl Env Microbiology, Sep. 1997, vol. 63, No. 9, pp. 3341-3344.
Jackson et al, Metabolic Engineering to Produce Sesquiterpenes in Yeast, Organ.Lett (2003) 5:1629-1632.
Hamano et al, Cloning of a Gene Cluster Encoding Enzymes Responsible for the Mevalonate Pathway from a Terpenoid-antibiotic-producing Streptomyces Strain. Biosci. Biotechnol. Biochem., (2001), 65 (7), 1627-1635.
Kuzuyama et al. Heterologous Mevalonate Production in Streptomyces lividans TK23. Biosci. Biotechnol. Biochem. (2004), 68 (4), 931-934.
Kazuhiko et al. Production of mevalonate by a metabolically-engineered *Escherichia coli*. Biotechnology Lett (2004), vol. 26: 1487-1491.
Brock et al., On the mechanism of action of the antifungal agent propionate Propionyl-CoA inhibits glucose metabolism in *Aspergillus nidulans*., Eur. J. Biochem. 271, 3227-3241 (2004).
Choi et al, High-Level Production of Poly(3-Hydroxybutyrate-co-3-Hydroxyvalerate) by Fed-Batch Culture of Recombinant *Escherichia coli*. Appl. Env. Microbiol. (Oct. 1999), vol. 65, No. 10, pp. 4363-4368.

(Continued)

*Primary Examiner* — Nashaat Nashed
(74) *Attorney, Agent, or Firm* — Robin C. Chiang; Lawrence Berkeley National Laboratory

(57) ABSTRACT

The invention provides for a method for producing a 5-carbon alcohol in a genetically modified host cell. In one embodiment, the method comprises culturing a genetically modified host cell which expresses a first enzyme capable of catalyzing the dephosphorylation of an isopentenyl pyrophosphate (IPP) or dimethylallyl diphosphate (DMAPP), such as a *Bacillus subtilis* phosphatase (YhfR), under a suitable condition so that 5-carbon alcohol is 3-methyl-2-buten-1-ol and/or 3-methyl-3-buten-1-ol is produced. Optionally, the host cell may further comprise a second enzyme capable of reducing a 3-methyl-2-buten-1-ol to 3-methyl-butan-1-ol, such as a reductase.

21 Claims, 3 Drawing Sheets

OTHER PUBLICATIONS

Parke et al, Toxicity Caused by Hydroxycinnamoyl-Coenzyme A Thioester Accumulation in Mutants of *Acinetobacter* sp. Strain ADP1., Appl. Env. Microbiol. (May 2004), vol. 70, No. 5, pp. 2974-2983.

Subrahmanyam et al., Overproduction of a Functional Fatty Acid Biosynthesis Enzyme Blocks Fatty Acid Synthesis in *Escherichia coli*.; J. Bacteriology (Sep. 1998), vol. 180, No. 17, pp. 4596-4602.

Murli et al., Metabolic engineering of *Escherichia coli* for improved 6-deoxyerythronolide B production. J Ind Microbiol Biotechnol (2003) 30: 500-509.

Ro et al., Production of the antimalarial drug precursor artemisinic acid in engineered yeast, Nature 2006, 440:940.

Reiling et al., Mono and Diterpene Production in *Escherichia coli*. Biotechnol. Bioeng. 2004, 87: 200-212.

Song, Lisheng. A Soluble Form of Phosphatase in *Saccharomyces cerevisiae* Capable of Converting Farnesyl Diphosphate Into E,E-Farnesol. Appl. Biochem. Biotechnol. (2006) 128: 149-157.

Takami et al., Complete genome sequence of the alkaliphilic bacterium *Bacillus halodurans* and genomic sequence comparison with *Bacillus subtilis*. Nucleic Acids Research, 2000, vol. 28, No. 21, pp. 4317-4331.

Kunst et al. The complete genome sequence of the Gram-positive bacterium *Bacillus subtilis*; Nature (1997), 390:249-256.

Pearson et al., Journal of Bateriology (2000) 182: 4121-4123.

Mildvan et al. Structures and mechanisms of Nudix hydrolases., Arch. Biochem. Biophysics (2005) 433: 129.

Allen et al., Phosporyl group transfer: evolution of a catalytic scaffold. Trends Biochem. Sci. (2004) 29: 495.

Rigden et al., Structures of Phosphate and Trivanadate Complexes of *Bacillus stearothermophilus* Phosphatase PhoE: Structural and Functional Analysis in the Cofactordependent Phosphoglycerate Mutase Superfamily. J. Mol. Biol. (2003) 325: 411.

McLennan, A.G., The Nudix hydrolase superfamily. Cellular and Mol. Life Sci. (2006), vol. 63, No. 2, pp. 123-143.

Kuznetsova et al., Genome-wide Analysis of Substrate Specificities of the *Escherichia coli* Haloacid Dehalogenase-like Phosphatase Family. J. Biol. Chem. (2006) vol. 281, No. 47, pp. 36149-36161.

Ward et al., Reductive biotransformations of organic compounds by cells or enzymes of yeast. Enzyme Microb. Technol., 1990, vol. 12, pp. 482-493.

Rodriguez et al., Highly Stereoselective Reagents for Beta-Keto Ester Reductions by Genetic Engineering of Baker's Yeast., J. Am. Chem. Soc. (2001), vol. 123, No. 8, pp. 1547-1555.

King et al., Biotransformation of monoterpene alcohols by *Saccharomyces cerevisiae*, *Torulaspora delbrueckii* and *Kluyveromyces lactis*. Yeast (2000) 16: 499-506.

Williams et al., 'New uses for an Old Enzyme' —The Old Yellow Enzyme family of flavoenzymes., Microbiology (2002) 148:1607-1614.

Larroy et al., Characterization of a *Saccharomyces cerevisiae* NADP(H)-dependent alcohol dehydrogenase (ADHVII), a member of the cinnamyl alcohol dehydrogenase family. Eur. J. Biochem. 269, 5738-5745 (2002).

Dickinson et al., The activity of yeast ADH I and ADH II with long-chain alcohols and diols. Chemico-Biological Interactions (2001) vol. 130-132, pp. 417-423.

International Preliminary Report on Patentability and Written Opinion of the ISA, PCT/US2008/068831; mailed Oct. 9, 2008.

International Application Published under the Patent Cooperation Treaty, WO 2009/006429A1, Jan. 8, 2009, and ISR.

SEQUENCE LISTING

```
<160> NUMBER OF SEQ ID NOS: 74

<210> SEQ ID NO 1
<211> LENGTH: 4
<212> TYPE: PRT
<213> ORGANISM: Artificial Sequence
<220> FEATURE:
<223> OTHER INFORMATION: conserved phosphatase enzyme sequence

<400> SEQUENCE: 1

Arg His Gly Glu
1

<210> SEQ ID NO 2
<211> LENGTH: 5
<212> TYPE: PRT
<213> ORGANISM: Artificial Sequence
<220> FEATURE:
<223> OTHER INFORMATION: conserved phosphatase enzyme sequence

<400> SEQUENCE: 2

Arg His Gly Glu Thr
1               5

<210> SEQ ID NO 3
<211> LENGTH: 5
<212> TYPE: PRT
<213> ORGANISM: Artificial Sequence
<220> FEATURE:
<223> OTHER INFORMATION: conserved phosphatase enzyme sequence

<400> SEQUENCE: 3

Arg His Gly Glu Ser
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: conserved phosphatase enzyme sequence

<400> SEQUENCE: 4

Arg His Gly Glu Thr Trp Asn
 1               5

<210> SEQ ID NO 5
<211> LENGTH: 7
<212> TYPE: PRT
<213> ORGANISM: Artificial Sequence
<220> FEATURE:
<223> OTHER INFORMATION: conserved phosphatase enzyme sequence

<400> SEQUENCE: 5

Arg His Gly Glu Ser Trp Asn
 1               5

<210> SEQ ID NO 6
<211> LENGTH: 7
<212> TYPE: PRT
<213> ORGANISM: Artificial Sequence
<220> FEATURE:
<223> OTHER INFORMATION: conserved phosphatase enzyme sequence

<400> SEQUENCE: 6

Arg His Gly Glu Thr Gly Asn
 1               5

<210> SEQ ID NO 7
<211> LENGTH: 7
<212> TYPE: PRT
<213> ORGANISM: Artificial Sequence
<220> FEATURE:
<223> OTHER INFORMATION: conserved phosphatase enzyme sequence

<400> SEQUENCE: 7

Arg His Gly Glu Ser Gly Asn
 1               5

<210> SEQ ID NO 8
<211> LENGTH: 8
<212> TYPE: PRT
<213> ORGANISM: Artificial Sequence
<220> FEATURE:
<223> OTHER INFORMATION: conserved phosphatase enzyme sequence
<221> NAME/KEY: VARIANT
<222> LOCATION: (4)...(7)
<223> OTHER INFORMATION: Xaa = any amino acid

<400> SEQUENCE: 8

Arg His Gly Xaa Xaa Xaa Xaa Asn
 1               5

<210> SEQ ID NO 9
<211> LENGTH: 143
<212> TYPE: PRT
<213> ORGANISM: Artificial Sequence
<220> FEATURE:
<223> OTHER INFORMATION: conserved phosphatase enzyme sequence
<221> NAME/KEY: VARIANT
<222> LOCATION: (5)...(7)
<223> OTHER INFORMATION: Xaa = any amino acid
<221> NAME/KEY: VARIANT
```

```
<222> LOCATION: (9)...(50)
<223> OTHER INFORMATION: Xaa = any amino acid
<221> NAME/KEY: VARIANT
<222> LOCATION: (52)...(74)
<223> OTHER INFORMATION: Xaa = any amino acid
<221> NAME/KEY: VARIANT
<222> LOCATION: (76)...(142)
<223> OTHER INFORMATION: Xaa = any amino acid; Xaa 132 through Xaa 142
      can be present or absent

<400> SEQUENCE: 9

Arg His Gly Glu Xaa Xaa Xaa Asn Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Arg Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Glu Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa His
    130                 135                 140

<210> SEQ ID NO 10
<211> LENGTH: 15
<212> TYPE: PRT
<213> ORGANISM: Artificial Sequence
<220> FEATURE:
<223> OTHER INFORMATION: conserved phosphatase enzyme sequence
<221> NAME/KEY: VARIANT
<222> LOCATION: (5)...(7)
<223> OTHER INFORMATION: Xaa = any amino acid
<221> NAME/KEY: VARIANT
<222> LOCATION: (9)...(13)
<223> OTHER INFORMATION: Xaa = any amino acid

<400> SEQUENCE: 10

Arg His Gly Glu Xaa Xaa Xaa Asn Xaa Xaa Xaa Xaa Gln Gly
 1               5                   10              15

<210> SEQ ID NO 11
<211> LENGTH: 25
<212> TYPE: PRT
<213> ORGANISM: Artificial Sequence
<220> FEATURE:
<223> OTHER INFORMATION: conserved phosphatase enzyme sequence
<221> NAME/KEY: VARIANT
<222> LOCATION: (4)...(7)
<223> OTHER INFORMATION: Xaa = any amino acid
<221> NAME/KEY: VARIANT
<222> LOCATION: (9)...(17)
<223> OTHER INFORMATION: Xaa = any amino acid; Xaa 16 through Xaa 17 can
      be present or absent
<221> NAME/KEY: VARIANT
<222> LOCATION: (19)...(20)
<223> OTHER INFORMATION: Xaa = any amino acid
<221> NAME/KEY: VARIANT
<222> LOCATION: (22)...(24)
<223> OTHER INFORMATION: Xaa = any amino acid

<400> SEQUENCE: 11
```

```
Arg His Gly Xaa Xaa Xaa Xaa Asn Xaa Xaa Xaa Xaa Xaa Xaa Xaa
1               5                   10                  15

Xaa Asp Xaa Xaa Leu Xaa Xaa Xaa Gly
            20                  25

<210> SEQ ID NO 12
<211> LENGTH: 24
<212> TYPE: PRT
<213> ORGANISM: Artificial Sequence
<220> FEATURE:
<223> OTHER INFORMATION: consensus Nudix box motif
<221> NAME/KEY: VARIANT
<222> LOCATION: (2)...(6)
<223> OTHER INFORMATION: Xaa = any amino acid
<221> NAME/KEY: VARIANT
<222> LOCATION: (8)...(12)
<223> OTHER INFORMATION: Xaa = any amino acid
<221> NAME/KEY: VARIANT
<222> LOCATION: (13)...(13)
<223> OTHER INFORMATION: Xaa = any aliphatic, hydrophobic amino acid
<221> NAME/KEY: VARIANT
<222> LOCATION: (15)...(15)
<223> OTHER INFORMATION: Xaa = any amino acid
<221> NAME/KEY: VARIANT
<222> LOCATION: (18)...(19)
<223> OTHER INFORMATION: Xaa = any amino acid
<221> NAME/KEY: VARIANT
<222> LOCATION: (22)...(22)
<223> OTHER INFORMATION: Xaa = any amino acid
<221> NAME/KEY: VARIANT
<222> LOCATION: (24)...(24)
<223> OTHER INFORMATION: Xaa = any aliphatic, hydrophobic amino acid

<400> SEQUENCE: 12

Gly Xaa Xaa Xaa Xaa Xaa Glu Xaa Xaa Xaa Xaa Xaa Xaa Ala Xaa Arg
1               5                   10                  15

Glu Xaa Xaa Glu Glu Xaa Gly Xaa
            20

<210> SEQ ID NO 13
<211> LENGTH: 22
<212> TYPE: PRT
<213> ORGANISM: Artificial Sequence
<220> FEATURE:
<223> OTHER INFORMATION: conserved Nudix box motif
<221> NAME/KEY: VARIANT
<222> LOCATION: (2)...(6)
<223> OTHER INFORMATION: Xaa = any amino acid
<221> NAME/KEY: VARIANT
<222> LOCATION: (8)...(13)
<223> OTHER INFORMATION: Xaa = any amino acid
<221> NAME/KEY: VARIANT
<222> LOCATION: (16)...(17)
<223> OTHER INFORMATION: Xaa = any amino acid
<221> NAME/KEY: VARIANT
<222> LOCATION: (20)...(20)
<223> OTHER INFORMATION: Xaa = any amino acid
<221> NAME/KEY: VARIANT
<222> LOCATION: (22)...(22)
<223> OTHER INFORMATION: Xaa = any aliphatic, hyrodphobic amino acid

<400> SEQUENCE: 13

Gly Xaa Xaa Xaa Xaa Xaa Glu Xaa Xaa Xaa Xaa Xaa Xaa Arg Glu Xaa
1               5                   10                  15

Xaa Glu Glu Xaa Gly Xaa
            20

<210> SEQ ID NO 14
<211> LENGTH: 11
<212> TYPE: PRT
<213> ORGANISM: Artificial Sequence
```

```
-continued

<220> FEATURE:
<223> OTHER INFORMATION: conserved OYE family consensus sequence
<221> NAME/KEY: VARIANT
<222> LOCATION: (3)...(3)
<223> OTHER INFORMATION: Xaa = any amino acid

<400> SEQUENCE: 14

Ser Asn Xaa Arg Thr Asp Glu Tyr Gly Gly Ser
1               5                   10

<210> SEQ ID NO 15
<211> LENGTH: 11
<212> TYPE: PRT
<213> ORGANISM: Artificial Sequence
<220> FEATURE:
<223> OTHER INFORMATION: conserved OYE family consensus sequence
<221> NAME/KEY: VARIANT
<222> LOCATION: (3)...(3)
<223> OTHER INFORMATION: Xaa = any amino acid

<400> SEQUENCE: 15

Ser Asn Xaa Arg Thr Asp Glu Tyr Gly Gly Thr
1               5                   10

<210> SEQ ID NO 16
<211> LENGTH: 15
<212> TYPE: PRT
<213> ORGANISM: Artificial Sequence
<220> FEATURE:
<223> OTHER INFORMATION: zinc-dependent alcohol dehydrogenase consensus
      sequence
<221> NAME/KEY: VARIANT
<222> LOCATION: (4)...(5)
<223> OTHER INFORMATION: Xaa = any amino acid
<221> NAME/KEY: VARIANT
<222> LOCATION: (7)...(11)
<223> OTHER INFORMATION: Xaa = any amino acid
<221> NAME/KEY: VARIANT
<222> LOCATION: (13)...(14)
<223> OTHER INFORMATION: Xaa = any amino acid

<400> SEQUENCE: 16

Gly His Glu Xaa Xaa Gly Xaa Xaa Xaa Xaa Xaa Gly Xaa Xaa Ile
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: zinc-dependent alcohol dehydrogenase consensus
      sequence
<221> NAME/KEY: VARIANT
<222> LOCATION: (4)...(5)
<223> OTHER INFORMATION: Xaa =  any amino acid
<221> NAME/KEY: VARIANT
<222> LOCATION: (7)...(11)
<223> OTHER INFORMATION: Xaa = any amino acid
<221> NAME/KEY: VARIANT
<222> LOCATION: (13)...(14)
<223> OTHER INFORMATION: Xaa =  any amino acid

<400> SEQUENCE: 17

Gly His Glu Xaa Xaa Gly Xaa Xaa Xaa Xaa Xaa Gly Xaa Xaa Val
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: zinc-dependent alcohol dehydrogenase consensus
```

```
                              sequence
<221> NAME/KEY: VARIANT
<222> LOCATION: (4)...(5)
<223> OTHER INFORMATION: Xaa = any amino acid
<221> NAME/KEY: VARIANT
<222> LOCATION: (7)...(11)
<223> OTHER INFORMATION: Xaa = any amino acid
<221> NAME/KEY: VARIANT
<222> LOCATION: (13)...(14)
<223> OTHER INFORMATION: Xaa = any amino acid

<400> SEQUENCE: 18

Gly His Glu Xaa Xaa Gly Xaa Xaa Xaa Xaa Xaa Gly Xaa Xaa Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: zinc-dependent alcohol dehydrogenase consensus
                              sequence
<221> NAME/KEY: VARIANT
<222> LOCATION: (4)...(5)
<223> OTHER INFORMATION: Xaa = any amino acid
<221> NAME/KEY: VARIANT
<222> LOCATION: (7)...(11)
<223> OTHER INFORMATION: Xaa = any amino acid
<221> NAME/KEY: VARIANT
<222> LOCATION: (13)...(14)
<223> OTHER INFORMATION: Xaa = any amino acid

<400> SEQUENCE: 19

Gly His Glu Xaa Xaa Gly Xaa Xaa Xaa Xaa Xaa Gly Xaa Xaa Cys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: zinc-dependent alcohol dehydrogenase consensus
                              sequence
<221> NAME/KEY: VARIANT
<222> LOCATION: (4)...(5)
<223> OTHER INFORMATION: Xaa = any amino acid
<221> NAME/KEY: VARIANT
<222> LOCATION: (7)...(11)
<223> OTHER INFORMATION: Xaa = any amino acid
<221> NAME/KEY: VARIANT
<222> LOCATION: (13)...(14)
<223> OTHER INFORMATION: Xaa = any amino acid

<400> SEQUENCE: 20

Gly His Glu Xaa Xaa Gly Xaa Xaa Xaa Xaa Xaa Gly Xaa Xaa Ser
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: zinc-dependent alcohol dehydrogenase consensus
                              sequence
<221> NAME/KEY: VARIANT
<222> LOCATION: (4)...(5)
<223> OTHER INFORMATION: Xaa = any amino acid
<221> NAME/KEY: VARIANT
<222> LOCATION: (7)...(11)
<223> OTHER INFORMATION: Xaa = any amino acid
<221> NAME/KEY: VARIANT
<222> LOCATION: (13)...(14)
<223> OTHER INFORMATION: Xaa = any amino acid
```

```
<400> SEQUENCE: 21

Gly His Glu Xaa Xaa Gly Xaa Xaa Xaa Xaa Ala Xaa Xaa Ile
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: zinc-dependent alcohol dehydrogenase consensus
      sequence
<221> NAME/KEY: VARIANT
<222> LOCATION: (4)...(5)
<223> OTHER INFORMATION: Xaa = any amino acid
<221> NAME/KEY: VARIANT
<222> LOCATION: (7)...(11)
<223> OTHER INFORMATION: Xaa = any amino acid
<221> NAME/KEY: VARIANT
<222> LOCATION: (13)...(14)
<223> OTHER INFORMATION: Xaa = any amino acid

<400> SEQUENCE: 22

Gly His Glu Xaa Xaa Gly Xaa Xaa Xaa Xaa Ala Xaa Xaa Val
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: zinc-dependent alcohol dehydrogenase consensus
      sequence
<221> NAME/KEY: VARIANT
<222> LOCATION: (4)...(5)
<223> OTHER INFORMATION: Xaa = any amino acid
<221> NAME/KEY: VARIANT
<222> LOCATION: (7)...(11)
<223> OTHER INFORMATION: Xaa = any amino acid
<221> NAME/KEY: VARIANT
<222> LOCATION: (13)...(14)
<223> OTHER INFORMATION: Xaa = any amino acid

<400> SEQUENCE: 23

Gly His Glu Xaa Xaa Gly Xaa Xaa Xaa Xaa Ala Xaa Xaa Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: zinc-dependent alcohol dehydrogenase consensus
      sequence
<221> NAME/KEY: VARIANT
<222> LOCATION: (4)...(5)
<223> OTHER INFORMATION: Xaa = any amino acid
<221> NAME/KEY: VARIANT
<222> LOCATION: (7)...(11)
<223> OTHER INFORMATION: Xaa = any amino acid
<221> NAME/KEY: VARIANT
<222> LOCATION: (13)...(14)
<223> OTHER INFORMATION: Xaa = any amino acid

<400> SEQUENCE: 24

Gly His Glu Xaa Xaa Gly Xaa Xaa Xaa Xaa Ala Xaa Xaa Cys
1               5                   10                  15

<210> SEQ ID NO 25
<211> LENGTH: 15
<212> TYPE: PRT
<213> ORGANISM: Artificial Sequence
<220> FEATURE:
```

```
<223> OTHER INFORMATION: zinc-dependent alcohol dehydrogenase consensus
      sequence
<221> NAME/KEY: VARIANT
<222> LOCATION: (4)...(5)
<223> OTHER INFORMATION: Xaa = any amino acid
<221> NAME/KEY: VARIANT
<222> LOCATION: (7)...(11)
<223> OTHER INFORMATION: Xaa = any amino acid
<221> NAME/KEY: VARIANT
<222> LOCATION: (13)...(14)
<223> OTHER INFORMATION: Xaa = any amino acid

<400> SEQUENCE: 25

Gly His Glu Xaa Xaa Gly Xaa Xaa Xaa Xaa Xaa Ala Xaa Xaa Ser
  1               5                  10                  15

<210> SEQ ID NO 26
<211> LENGTH: 34
<212> TYPE: DNA
<213> ORGANISM: Artificial Sequence
<220> FEATURE:
<223> OTHER INFORMATION: Synthetic YHR179w primer 1

<400> SEQUENCE: 26
aaccgtcgac atgccatttg ttaaggactt taag                               34

<210> SEQ ID NO 27
<211> LENGTH: 40
<212> TYPE: DNA
<213> ORGANISM: Artificial Sequence
<220> FEATURE:
<223> OTHER INFORMATION: Synthetic YHR179w primer 2

<400> SEQUENCE: 27
taacgctagc ttaattttg tcccaaccga gttttagagc                          40

<210> SEQ ID NO 28
<211> LENGTH: 35
<212> TYPE: DNA
<213> ORGANISM: Artificial Sequence
<220> FEATURE:
<223> OTHER INFORMATION: Synthetic YPL171c primer 1

<400> SEQUENCE: 28
aaccgtcgac atgccatttg taaaaggttt tgagc                              35

<210> SEQ ID NO 29
<211> LENGTH: 37
<212> TYPE: DNA
<213> ORGANISM: Artificial Sequence
<220> FEATURE:
<223> OTHER INFORMATION: Synthetic YPL171c primer 2

<400> SEQUENCE: 29
taacgctagc tcagttcttg ttccaaccta aatctac                            37

<210> SEQ ID NO 30
<211> LENGTH: 33
<212> TYPE: DNA
<213> ORGANISM: Artificial Sequence
<220> FEATURE:
<223> OTHER INFORMATION: Synthetic YOR120w primer 1

<400> SEQUENCE: 30
aaccggatcc atgcctgcta ctttacatga ttc                                33

<210> SEQ ID NO 31
<211> LENGTH: 33
```

```
<212> TYPE: DNA
<213> ORGANISM: Artificial Sequence
<220> FEATURE:
<223> OTHER INFORMATION: Synthetic YOR120w primer 2

<400> SEQUENCE: 31
taacctcgag ttacttgaat acttcgaaag gag                              33

<210> SEQ ID NO 32
<211> LENGTH: 30
<212> TYPE: DNA
<213> ORGANISM: Artificial Sequence
<220> FEATURE:
<223> OTHER INFORMATION: Synthetic YDR368w primer 1

<400> SEQUENCE: 32
aaccgtcgac atgcctgcta cgttaaagaa                                  30

<210> SEQ ID NO 33
<211> LENGTH: 29
<212> TYPE: DNA
<213> ORGANISM: Artificial Sequence
<220> FEATURE:
<223> OTHER INFORMATION: Synthetic YDR368w primer 2

<400> SEQUENCE: 33
taacctcgag tcattggaaa attgggaag                                   29

<210> SEQ ID NO 34
<211> LENGTH: 30
<212> TYPE: DNA
<213> ORGANISM: Artificial Sequence
<220> FEATURE:
<223> OTHER INFORMATION: Synthetic YBR149w primer 1

<400> SEQUENCE: 34
aaccggatcc atgtcttctt cagtagcctc                                  30

<210> SEQ ID NO 35
<211> LENGTH: 32
<212> TYPE: DNA
<213> ORGANISM: Artificial Sequence
<220> FEATURE:
<223> OTHER INFORMATION: Synthetic YBR149w primer 2

<400> SEQUENCE: 35
taacgctagc ttaatacttt aaattgtcca ag                               32

<210> SEQ ID NO 36
<211> LENGTH: 32
<212> TYPE: DNA
<213> ORGANISM: Artificial Sequence
<220> FEATURE:
<223> OTHER INFORMATION: Synthetic YHR104w primer 1

<400> SEQUENCE: 36
aaccggatcc atgtcttcac tggttactct ta                               32

<210> SEQ ID NO 37
<211> LENGTH: 29
<212> TYPE: DNA
<213> ORGANISM: Artificial Sequence
<220> FEATURE:
<223> OTHER INFORMATION: Synthetic YHR104w primer 2

<400> SEQUENCE: 37
taacctcgag tcaggcaaaa gtggggaat                                   29
```

<210> SEQ ID NO 38
<211> LENGTH: 31
<212> TYPE: DNA
<213> ORGANISM: Artificial Sequence
<220> FEATURE:
<223> OTHER INFORMATION: Synthetic YDL124w primer 1

<400> SEQUENCE: 38
aaccggatcc atgtcatttc accaacagtt c            31

<210> SEQ ID NO 39
<211> LENGTH: 29
<212> TYPE: DNA
<213> ORGANISM: Artificial Sequence
<220> FEATURE:
<223> OTHER INFORMATION: Synthetic YDL124w primer 2

<400> SEQUENCE: 39
taacctcgag ttatactttt tgagcagcg              29

<210> SEQ ID NO 40
<211> LENGTH: 32
<212> TYPE: DNA
<213> ORGANISM: Artificial Sequence
<220> FEATURE:
<223> OTHER INFORMATION: Synthetic YJR096w primer 1

<400> SEQUENCE: 40
aaccggatcc atggttccta agttttacaa ac           32

<210> SEQ ID NO 41
<211> LENGTH: 31
<212> TYPE: DNA
<213> ORGANISM: Artificial Sequence
<220> FEATURE:
<223> OTHER INFORMATION: Synthetic YJR096w primer 2

<400> SEQUENCE: 41
taacctcgag ttatggcgcg tctgtgcatt c            31

<210> SEQ ID NO 42
<211> LENGTH: 32
<212> TYPE: DNA
<213> ORGANISM: Artificial Sequence
<220> FEATURE:
<223> OTHER INFORMATION: Synthetic YIR036c primer 1

<400> SEQUENCE: 42
aaccggatcc atgggcaagg ttattttgat ta           32

<210> SEQ ID NO 43
<211> LENGTH: 33
<212> TYPE: DNA
<213> ORGANISM: Artificial Sequence
<220> FEATURE:
<223> OTHER INFORMATION: Synthetic YIR036c primer 2

<400> SEQUENCE: 43
taacgctagc ctagccctgc accggcccca gtc          33

<210> SEQ ID NO 44
<211> LENGTH: 32
<212> TYPE: DNA
<213> ORGANISM: Artificial Sequence
<220> FEATURE:
<223> OTHER INFORMATION: Synthetic YMR226c primer 1

```
<400> SEQUENCE: 44
aaccggatcc atgtcccaag gtagaaaagc tg                                       32

<210> SEQ ID NO 45
<211> LENGTH: 35
<212> TYPE: DNA
<213> ORGANISM: Artificial Sequence
<220> FEATURE:
<223> OTHER INFORMATION: Synthetic YMR226c primer 2

<400> SEQUENCE: 45
taacgctagc ttatccacgg aagatatgat gaggt                                    35

<210> SEQ ID NO 46
<211> LENGTH: 32
<212> TYPE: DNA
<213> ORGANISM: Artificial Sequence
<220> FEATURE:
<223> OTHER INFORMATION: Synthetic YOL151w primer 1

<400> SEQUENCE: 46
aaccggatcc atgtcagttt tcgtttcagg tg                                       32

<210> SEQ ID NO 47
<211> LENGTH: 36
<212> TYPE: DNA
<213> ORGANISM: Artificial Sequence
<220> FEATURE:
<223> OTHER INFORMATION: Synthetic YOL151w primer 2

<400> SEQUENCE: 47
taacctcgag ttatattctg ccctcaaatt ttaaaa                                   36

<210> SEQ ID NO 48
<211> LENGTH: 34
<212> TYPE: DNA
<213> ORGANISM: Artificial Sequence
<220> FEATURE:
<223> OTHER INFORMATION: Synthetic YGL157w primer 1

<400> SEQUENCE: 48
aaccggatcc atgactactg ataccactgt tttc                                     34

<210> SEQ ID NO 49
<211> LENGTH: 28
<212> TYPE: DNA
<213> ORGANISM: Artificial Sequence
<220> FEATURE:
<223> OTHER INFORMATION: Synthetic YGL157w primer 2

<400> SEQUENCE: 49
taacctcgag ttaggcttca ttttgaac                                            28

<210> SEQ ID NO 50
<211> LENGTH: 29
<212> TYPE: DNA
<213> ORGANISM: Artificial Sequence
<220> FEATURE:
<223> OTHER INFORMATION: Synthetic YDR541c primer 1

<400> SEQUENCE: 50
aaccggatcc atgtctaata cagttctag                                           29

<210> SEQ ID NO 51
<211> LENGTH: 32
```

-continued

<212> TYPE: DNA
<213> ORGANISM: Artificial Sequence
<220> FEATURE:
<223> OTHER INFORMATION: Synthetic YDR541c primer 2

<400> SEQUENCE: 51
aaccggatcc tcataatctg ttctccttct tc                                32

<210> SEQ ID NO 52
<211> LENGTH: 32
<212> TYPE: DNA
<213> ORGANISM: Artificial Sequence
<220> FEATURE:
<223> OTHER INFORMATION: Synthetic YGL039w primer 1

<400> SEQUENCE: 52
aaccgtcgac atgactactg aaaaaaccgt tg                                32

<210> SEQ ID NO 53
<211> LENGTH: 42
<212> TYPE: DNA
<213> ORGANISM: Artificial Sequence
<220> FEATURE:
<223> OTHER INFORMATION: Synthetic YGL039w primer 2

<400> SEQUENCE: 53
taacgctagc ttagctttta ctttgaactt ctagtaattg cg                     42

<210> SEQ ID NO 54
<211> LENGTH: 31
<212> TYPE: DNA
<213> ORGANISM: Artificial Sequence
<220> FEATURE:
<223> OTHER INFORMATION: Synthetic YAL060w primer 1

<400> SEQUENCE: 54
aaccggatcc atgagagctt tggcatattt c                                 31

<210> SEQ ID NO 55
<211> LENGTH: 29
<212> TYPE: DNA
<213> ORGANISM: Artificial Sequence
<220> FEATURE:
<223> OTHER INFORMATION: Synthetic YAL060w primer 2

<400> SEQUENCE: 55
taacctcgag ttacttcatt tcaccgtga                                    29

<210> SEQ ID NO 56
<211> LENGTH: 30
<212> TYPE: DNA
<213> ORGANISM: Artificial Sequence
<220> FEATURE:
<223> OTHER INFORMATION: Synthetic YLR070c primer 1

<400> SEQUENCE: 56
aaccggatcc atgactgact taactacaca                                   30

<210> SEQ ID NO 57
<211> LENGTH: 32
<212> TYPE: DNA
<213> ORGANISM: Artificial Sequence
<220> FEATURE:
<223> OTHER INFORMATION: Synthetic YLR070c primer 2

<400> SEQUENCE: 57
taacctcgag tcattccggg ccctcaatga tc                                32

<210> SEQ ID NO 58
<211> LENGTH: 28
<212> TYPE: DNA
<213> ORGANISM: Artificial Sequence
<220> FEATURE:
<223> OTHER INFORMATION: Synthetic YGL185c primer 1

<400> SEQUENCE: 58
aaccggatcc atgtgcgatt ctcctgca                                28

<210> SEQ ID NO 59
<211> LENGTH: 33
<212> TYPE: DNA
<213> ORGANISM: Artificial Sequence
<220> FEATURE:
<223> OTHER INFORMATION: Synthetic YGL185c primer 2

<400> SEQUENCE: 59
taacctcgag tcaaactaca cgggagaaat gct                          33

<210> SEQ ID NO 60
<211> LENGTH: 34
<212> TYPE: DNA
<213> ORGANISM: Artificial Sequence
<220> FEATURE:
<223> OTHER INFORMATION: Synthetic YNL274c primer 1

<400> SEQUENCE: 60
aaccggatcc atgagtaaga aaccaattgt tttg                         34

<210> SEQ ID NO 61
<211> LENGTH: 31
<212> TYPE: DNA
<213> ORGANISM: Artificial Sequence
<220> FEATURE:
<223> OTHER INFORMATION: Synthetic YNL274c primer 2

<400> SEQUENCE: 61
taacctcgag tcaaactaat ggcttagatt c                            31

<210> SEQ ID NO 62
<211> LENGTH: 35
<212> TYPE: DNA
<213> ORGANISM: Artificial Sequence
<220> FEATURE:
<223> OTHER INFORMATION: Synthetic YPL113c primer 1

<400> SEQUENCE: 62
aaccggatcc atgattactt caattgacat agcag                        35

<210> SEQ ID NO 63
<211> LENGTH: 36
<212> TYPE: DNA
<213> ORGANISM: Artificial Sequence
<220> FEATURE:
<223> OTHER INFORMATION: Synthetic YPL113c primer 2

<400> SEQUENCE: 63
taacgctagc tcagttgagc acatacttac catcac                       36

<210> SEQ ID NO 64
<211> LENGTH: 30
<212> TYPE: DNA
<213> ORGANISM: Artificial Sequence
<220> FEATURE:
<223> OTHER INFORMATION: Synthetic YCR107w primer 1

```
<400> SEQUENCE: 64
aaccggatcc atgattgggt ccgcgtccga                                         30

<210> SEQ ID NO 65
<211> LENGTH: 28
<212> TYPE: DNA
<213> ORGANISM: Artificial Sequence
<220> FEATURE:
<223> OTHER INFORMATION: Synthetic YCR107w primer 2

<400> SEQUENCE: 65
taacctcgag ctaaacatta ttcgtacc                                           28

<210> SEQ ID NO 66
<211> LENGTH: 32
<212> TYPE: DNA
<213> ORGANISM: Artificial Sequence
<220> FEATURE:
<223> OTHER INFORMATION: Synthetic YNL331c primer 1

<400> SEQUENCE: 66
aaccggatcc atgactgact tgtttaaacc tc                                      32

<210> SEQ ID NO 67
<211> LENGTH: 32
<212> TYPE: DNA
<213> ORGANISM: Artificial Sequence
<220> FEATURE:
<223> OTHER INFORMATION: Synthetic YNL331c primer 2

<400> SEQUENCE: 67
taacctcgag ctaattgtca aaagctatcc tg                                      32

<210> SEQ ID NO 68
<211> LENGTH: 34
<212> TYPE: DNA
<213> ORGANISM: Artificial Sequence
<220> FEATURE:
<223> OTHER INFORMATION: Synthetic YPL275w primer 1

<400> SEQUENCE: 68
aaccggatcc atggtggtca tcaataagca atta                                    34

<210> SEQ ID NO 69
<211> LENGTH: 36
<212> TYPE: DNA
<213> ORGANISM: Artificial Sequence
<220> FEATURE:
<223> OTHER INFORMATION: Synthetic YPL275w primer 2

<400> SEQUENCE: 69
taacctcgag ttatttcttc tgtccataag ctctgg                                  36

<210> SEQ ID NO 70
<211> LENGTH: 208
<212> TYPE: PRT
<213> ORGANISM: Bacillus stearothermophilus

<400> SEQUENCE: 70

Met Ala Thr Thr Leu Tyr Leu Thr Arg His Gly Glu Thr Lys Trp Asn
 1               5                  10                  15

Val Glu Arg Arg Met Gln Gly Trp Gln Asp Ser Pro Leu Thr Glu Lys
            20                  25                  30

Gly Arg Gln Asp Ala Met Arg Leu Gly Lys Arg Leu Glu Ala Val Glu
```

```
                35                  40                  45
Leu Ala Ala Ile Tyr Thr Ser Thr Ser Gly Arg Ala Leu Glu Thr Ala
 50                  55                  60
Glu Ile Val Arg Gly Gly Arg Leu Ile Pro Ile Tyr Gln Asp Glu Arg
 65                  70                  75                  80
Leu Arg Glu Ile His Leu Gly Asp Trp Glu Gly Lys Thr His Asp Glu
                 85                  90                  95
Ile Arg Gln Met Asp Pro Ile Ala Phe Asp His Phe Trp Asn Ala Pro
                100                 105                 110
His Leu Tyr Ala Pro Gln Arg Gly Glu Arg Phe Cys Asp Val Gln Gln
                115                 120                 125
Arg Ala Leu Glu Ala Val Gln Ser Ile Val Asp Arg His Glu Gly Glu
130                 135                 140
Thr Val Leu Ile Val Thr His Gly Val Val Leu Lys Thr Leu Met Ala
145                 150                 155                 160
Ala Phe Lys Asp Thr Pro Leu Asp His Leu Trp Ser Pro Pro Tyr Met
                165                 170                 175
Tyr Gly Thr Ser Val Thr Ile Ile Glu Val Asp Gly Gly Thr Phe His
                180                 185                 190
Val Ala Val Glu Gly Asp Val Ser His Ile Glu Glu Val Lys Glu Val
                195                 200                 205

<210> SEQ ID NO 71
<211> LENGTH: 207
<212> TYPE: PRT
<213> ORGANISM: Bacillus stearothermophilus

<400> SEQUENCE: 71

Met Ala Thr Thr Leu Tyr Leu Thr Arg His Gly Glu Thr Lys Trp Asn
  1               5                  10                  15
Val Glu Arg Arg Met Gln Gly Trp Gln Asp Ser Pro Leu Thr Glu Lys
                 20                  25                  30
Gly Arg Gln Asp Ala Met Arg Leu Gly Lys Arg Leu Glu Ala Val Glu
                 35                  40                  45
Leu Ala Ala Ile Tyr Thr Ser Thr Ser Gly Arg Ala Leu Glu Thr Ala
 50                  55                  60
Glu Ile Val Arg Gly Gly Arg Leu Ile Pro Ile Tyr Gln Asp Glu Arg
 65                  70                  75                  80
Leu Arg Glu Ile Tyr Leu Gly Asp Trp Glu Gly Lys Thr His Asp Glu
                 85                  90                  95
Ile Arg Gln Met Asp Pro Ile Ala Phe Asp His Phe Trp Asn Ala Pro
                100                 105                 110
His Leu Tyr Ala Pro Lys Arg Gly Glu Arg Phe Cys Asp Val Gln Gln
                115                 120                 125
Arg Ala Leu Glu Ala Val Gln Arg Ile Val Arg Arg His Glu Gly Glu
130                 135                 140
Thr Val Leu Ile Val Thr His Gly Val Val Leu Lys Thr Leu Val Ala
145                 150                 155                 160
Ala Phe Lys Gly Ala Pro Leu Asp His Leu Trp Ser Pro Pro Tyr Met
                165                 170                 175
Tyr Gly Thr Ser Val Thr Ile Val Glu Ala Gly Asp Gly Phe Arg Val
                180                 185                 190
Val Val Glu Gly Asp Ala Ser His Val Glu Glu Val Lys Glu Val
                195                 200                 205
```

<210> SEQ ID NO 72
<211> LENGTH: 205
<212> TYPE: PRT
<213> ORGANISM: Bacillus anthracis

<400> SEQUENCE: 72

```
Met Glu Val Lys Thr Thr Val Tyr Val Thr Arg His Gly Glu Thr Glu
  1               5                  10                  15
Trp Asn Val Ala Lys Arg Met Gln Gly Arg Lys Asn Ser Thr Leu Thr
                 20                  25                  30
Glu Asn Gly Ile Leu Gln Ala Lys Gln Leu Gly Glu Arg Met Lys Asp
             35                  40                  45
Leu Ser Ile His Ala Ile Tyr Ser Ser Pro Ser Glu Arg Thr Leu His
         50                  55                  60
Thr Ala Glu Leu Ile Lys Gly Glu Arg Asp Ile Pro Ile Ile Ala Asp
 65                  70                  75                  80
Glu His Phe Tyr Glu Ile Asn Met Gly Ile Trp Glu Gly Gln Thr Ile
                 85                  90                  95
Asp Asp Ile Glu Arg Gln Tyr Pro Asp Asp Ile Gln Leu Phe Trp Asn
            100                 105                 110
Glu Pro His Leu Phe Gln Ser Thr Ser Gly Glu Asn Phe Glu Ala Val
            115                 120                 125
His Lys Arg Val Ile Glu Gly Met Gln Leu Leu Leu Glu Lys His Lys
        130                 135                 140
Gly Glu Ser Ile Leu Ile Val Ser His Ala Ala Ala Lys Leu Leu
145                 150                 155                 160
Val Gly His Phe Ala Gly Ile Glu Ile Glu Asn Val Trp Asp Asp Pro
                165                 170                 175
Phe Met His Ser Ala Ser Leu Ser Ile Ile Glu Phe Gly Asp Gly Lys
            180                 185                 190
Gly Glu Val Lys Gln Phe Ala Asp Ile Ser His Pro Gln
            195                 200                 205
```

<210> SEQ ID NO 73
<211> LENGTH: 193
<212> TYPE: PRT
<213> ORGANISM: Bacillus subtilis

<400> SEQUENCE: 73

```
Met Thr Ala Val Cys Leu Val Arg His Gly Glu Thr Asp Trp Asn Leu
  1               5                  10                  15
Gln Gln Lys Cys Gln Gly Lys Thr Asp Ile Pro Leu Asn Ala Thr Gly
                 20                  25                  30
Glu Arg Gln Ala Arg Glu Thr Gly Glu Tyr Val Lys Asp Phe Ser Trp
             35                  40                  45
Asp Ile Ile Val Thr Ser Pro Leu Lys Arg Ala Lys Arg Thr Ala Glu
         50                  55                  60
Ile Ile Asn Glu Tyr Leu His Leu Pro Ile Val Glu Met Asp Asp Phe
 65                  70                  75                  80
Lys Glu Arg Asp Tyr Gly Asp Ala Glu Gly Met Pro Leu Glu Glu Arg
                 85                  90                  95
Thr Lys Arg Tyr Pro Asp Asn Ile Tyr Pro Asn Met Glu Thr Leu Glu
            100                 105                 110
Glu Leu Thr Asp Arg Leu Met Gly Gly Leu Ala Lys Val Asn Gln Ala
        115                 120                 125
Tyr Pro Asn Lys Lys Val Leu Ile Val Ala His Gly Ala Ala Ile His
        130                 135                 140
```

Ala Leu Leu Thr Glu Ile Ser Gly Gly Asp Pro Glu Leu Gln Ser Thr
145                 150                 155                 160

Arg Leu Val Asn Ala Cys Leu Ser Asn Ile Glu Phe Ala Glu Glu Lys
            165                 170                 175

Trp Arg Ile Lys Asp Tyr Asn Ile Asn Ser His Leu Ser Gly Phe Ile
            180                 185                 190

Lys

<210> SEQ ID NO 74
<211> LENGTH: 210
<212> TYPE: PRT
<213> ORGANISM: Bacillus halodurans

<400> SEQUENCE: 74

Met Asn Leu Tyr Leu Ile Arg His Gly Glu Ser Met Gly Asn Lys Leu
1               5                   10                  15

Gly Lys Ile Gln Gly Thr Glu Asp Phe Pro Leu Ser Pro Leu Gly Glu
            20                  25                  30

Lys Gln Ala Ala Glu Leu Gly Ser Tyr Phe Lys Ala Ile Pro Leu Asp
            35                  40                  45

Tyr Ile Tyr Ser Ser Asp Leu Thr Arg Ala His Glu Thr Ala Lys Ala
50                  55                  60

Ile Gly Gln Val Lys Gly Leu Pro Val Glu Ala Thr Ala Leu Ala Arg
65                  70                  75                  80

Glu Val His Leu Gly Pro Pro Gln Gly Lys Thr Arg Ala Glu Ile Tyr
                85                  90                  95

Glu His Tyr Pro Glu Thr Lys Lys Thr Thr Ile Leu Thr Ser Gly Ile
            100                 105                 110

Glu Gly Thr Glu Thr Val Glu Glu Leu Thr Lys Arg Cys Asn His Phe
            115                 120                 125

Arg Ser Glu Leu Leu Met Lys His Arg Gly Asn Val Ala Ile Val
            130                 135                 140

Ser His Gly Gly Phe Ile Ser Ile Phe Leu Met Tyr Leu Val Val Gly
145                 150                 155                 160

Glu Gln Trp Tyr Asn Phe His Arg Pro Phe Arg Ile Asp Asn Thr Asn
            165                 170                 175

Ile Thr Arg Val Glu Trp Thr Glu Asp Asp Arg Phe Phe Ile His Tyr
            180                 185                 190

Ile Gly Arg Asn Asn His Leu Glu Thr Leu Ser Asn Lys Ser Asn Thr
            195                 200                 205

Leu Leu
    210

HOST CELLS AND METHODS FOR PRODUCING 3-METHYL-2-BUTEN-1-OL, 3-METHYL-3-BUTEN-1-OL, AND 3-METHYL-BUTAN-1-OL

RELATED PATENT APPLICATIONS

This application claims priority as a continuation application to PCT International Application No. PCT/US2008/068831, filed Jun. 30, 2008, which claims priority to U.S. provisional application Ser. No. 60/947,285, filed Jun. 29, 2007, the contents of which are hereby incorporated by reference in their entireties.

STATEMENT OF GOVERNMENT SUPPORT

The invention described and claimed herein was made utilizing funds supplied by the U.S. Department of Energy under Contract No. DE-AC02-05CH11231. The government has certain rights in this invention.

FIELD OF THE INVENTION

The present invention is in the field of production of 5-carbon alcohol compounds, and in particular host cells that are genetically modified to produce 5-carbon alcohol compounds.

BACKGROUND OF THE INVENTION

Petroleum derived fuels have been the primary source of energy for over a hundred years. Petroleum is formed over millions of years in nature and is a non-renewable source of energy. A significant amount of research in biofuels has been ongoing for decades. Within this field, ethanol has been studied intensively as a gasoline substitute. However, the efficiency of ethanol as a fuel remains debatable. (Pimentel, *Natural Resources Research* (2005) 14:65; Farrell et al., *Science* (2006), 311:506).

The present invention provides methods for the biosynthesis of branched 5-carbon alcohols (branched-C5 alcohols) from the isoprenoid precursors isopentyl pyrophosphate (IPP) or dimethylallyl diphosphate (DMAPP).

Isoprenoids are compounds derived from the five-carbon molecule, IPP. Investigators have identified over 29,000 individual isoprenoid compounds, with new ones continuously being discovered. Isoprenoids are often isolated from natural products, such as plants and microorganisms, which use isopentenyl pyrophosphate as a basic building block to form relatively complex structures. Vital to living organisms, isoprenoids serve to maintain cellular fluidity and electron transport, as well as function as natural pesticides, to name just a few of their roles in vivo. Furthermore, the pharmaceutical and chemical communities use isoprenoids as pharmaceuticals, nutriceuticals, flavoring agents, and agricultural pest control agents. Given their importance in biological systems and usefulness in a broad range of applications, isoprenoids have been the focus of much attention by scientists.

Conventional means for producing isoprenoids include extraction from biological materials (e.g., plants, microbes, and animals) and partial or total organic synthesis in the laboratory. Such means, however, have generally been unsatisfactory as they involve the use of toxic solvents and provide a low yield of the desired isoprenoid. Recently, researchers have looked to the biosynthetic production of isoprenoids. U.S. Pat. No. 6,291,745 describes the production of limonene and other metabolites in plants. U.S. Pat. No. 6,190,895 describes nucleic acid sequences that code for the expression of 1-deoxyxylulose-5-phosphate synthase, an enzyme used in one biological pathway for the synthesis of isopentenyl pyrophosphate. U.S. Pat. No. 7,172,886 describes the cloning of genes for a mevalonate-isoprenoid pathway and synthesizing an isoprenoid or an isoprenoid precursor via the mevalonate pathway in a host cell. U.S. Pat. No. 7,183,089 describes a method for enhancing production of isoprenoid compounds in a host cell by modulating the level of hydroxymethylglutaryl-CoA (HMG-CoA) in the cell, such that the level of HMG-CoA is not toxic to the cell and does not substantially inhibit cell growth.

U.S. Pat. Nos. 5,460,949; 6,531,303; and 6,689,593; U.S. Pat. Pub. Nos. 2003/0148479; 2004/0029239; 2004/005678; 2004/0063182; 2004/0072323; 2004/0077039; 2004/0110259; and 2004/0194162; Martin et al. (2003) *Nat. Biotech.* 21(7):796-802; Polakowski et al. (1998) *Appl. Microbial. Biotechnol.* 49:67-71; Wilding et al. (2000) *J. Bacterial.* 182(15):4319-27; Donald et al. (1997) *Appl. Env. Microbial.* 63:3341-3344; Jackson et al. (2003) *Organ. Lett.* 5:1629-1632; Hamano et al. (2001) *Biosci. Biotechnol. Biochem.* 65:1627-1635; Kuzuyama (2004) *Biosci. Biotechnol. Biochem.* 68(4):931-934; Kazuhiko (2004) *Biotechnol. Lett.* 26:1487-1491; Brock et al. (2004) *Eur. J. Biochem.* 271: 3227-3241; Choi et al. (1999) *Appl. Environ. Microbiol.* 65:4363-4368; Parke et al. (2004) *Appl. Environ. Microbiol.* 70:2974-2983; Subrahmanyam et al. (1998) *J. Bacteriol.* 180: 4596-4602; Murli et al. (2003) *J. Ind Microbiol. Biotechnol.* 30:560-509. These references are hereby incorporated in their entireties by reference.

SUMMARY OF THE INVENTION

The present invention provides for a method of producing a 5-carbon alcohol in a genetically modified host cell. The method comprises culturing the genetically modified host cell under a suitable condition such that the culturing results in the genetically modified host cell producing a 5-carbon alcohol. The host cell comprises an enzyme capable of catalyzing the dephosphorylation of an isopentenyl pyrophosphate (IPP) or dimethylallyl diphosphate (DMAPP), and optionally a second enzyme capable of reducing a 3-methyl-2-buten-1-ol into 3-methyl-butan-1-ol. The 5-carbon alcohol is 3-methyl-2-buten-1-ol, 3-methyl-3-buten-1-ol, or 3-methyl-butan-1-ol, or any combination thereof.

The present invention also provides for a genetically modified host cell useful for the methods of the present invention.

The present invention further provides for an isolated 3-methyl-2-buten-1-ol, 3-methyl-3-buten-1-ol or 3-methyl-butan-1-ol produced from the method of the present invention.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figures 1, 2:
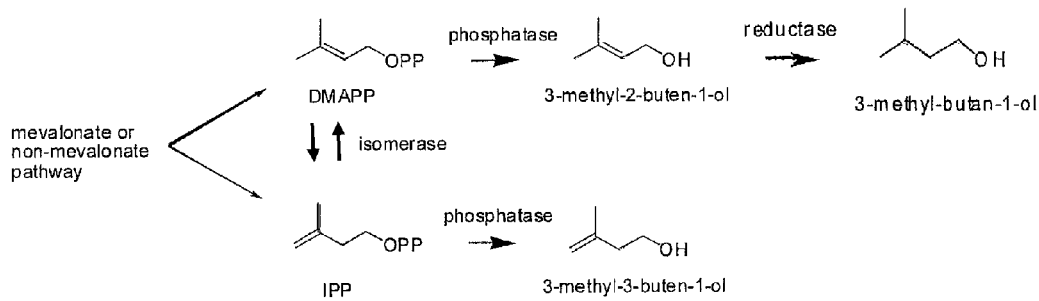
FIG. 1 shows the enzymatic pathway for producing 3-methyl-2-buten-1-ol, 3-methyl-3-buten-1-ol and 3-methyl-butan-1-ol.
FIG. 2 shows the sequence alignment of *Bacillus stearothermophilus* NGB101 YhfR (SEQ ID NO:70) with sequences of YhfR homologs in other *Bacillus* strains and species (SEQ ID NOs:71-74). Conserved amino acid residues are in bold and triangles mark amino acid residues lining the active site cleft of YhfR; filled triangles denote the conserved amino acid residues that form the catalytic core; and open triangles denote other positions.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In order to more fully appreciate the invention the following definitions are provided.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The term "mevalonate pathway" is used herein to refer to the pathway that converts acetyl-CoA to isopentenyl pyrophosphate through a mevalonate intermediate.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucicotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

"Alga," "algal," and "microalgae" or the like, refere to plants belonging to the subphylum Algae of the phylum Thallophyta. The algae are unicellular, photosynthetic, oxygenic algae and are non-parasitis plants without roots, stems, or leaves; they contain chlorophyll and have a great variety in size, from microscopic to large seaweeds. Green algae, belonging to Eukaryota—Viridiplantae—Chlorophyta—Chlorophyceae, can be used in the invention. However, algae useful in the invention may also be blue-green, red, or brown.

Introduction

The present invention provides methods for constructing a de novo synthetic pathway, in a genetically modified host cell, for the production of C5-isoprenyl alcohols and isopentanol using isopentenyl pyrophosphate (IPP) and dimethylallyl diphosphate (DMAPP) as substrates. These substrates can be derived from the non-mevalonate as well as mevalonate pathways.

In some embodiments of the invention, for the method for producing a 5-carbon alcohol in a genetically modified host cell, the method comprises: culturing a genetically modified host cell under a suitable condition, wherein the genetically modified host cell comprises a first enzyme capable of catalyzing the dephosphorylation of an isopentenyl pyrophosphate (IPP) or dimethylallyl diphosphate (DMAPP) to 3-methyl-3-buten-1-ol or 3-methyl-2-buten-1-ol, respectively, and optionally a second enzyme capable of reducing 3-methyl-2-buten-1-ol to 3-methyl-butan-1-ol.

In some embodiments of the invention, for the method for producing a 5-carbon alcohol in a genetically modified host cell, the method comprises: culturing a genetically modified host cell under a suitable condition, wherein the genetically modified host cell comprises an enzyme capable of catalyzing the dephosphorylation of an isopentenyl pyrophosphate (IPP) or dimethylallyl diphosphate (DMAPP) to 3-methyl-2-buten-1-ol or 3-methyl-3-buten-1-ol.

In some embodiments of the invention, for the method for producing a 5-carbon alcohol in a genetically modified host cell, the method comprises: culturing a genetically modified host cell under a suitable condition, wherein the genetically modified host cell comprises a first enzyme capable of catalyzing the dephosphorylation of a dimethylallyl diphosphate (DMAPP) to 3-methyl-2-buten-1-ol, and a second enzyme capable of reducing 3-methyl-2-buten-1-ol to 3-methyl-butan-1-ol.

In some embodiments the second enzyme capable of reducing 3-methyl-2-buten-1-ol to 3-methyl-butan-1-ol is a member of, or homologous to, the OYE family of reductases.

In some embodiments the OYE family member is OYE2 or a homolog. In some embodiments the OYE family member is OYE3 or a homolog.

In some embodiments of the invention, for the method for producing a 5-carbon alcohol in a genetically modified host cell, the method comprises: culturing a genetically modified host cell under a suitable condition, wherein the genetically modified host cell comprises a nucleic acid construct encoding an enzyme capable of catalyzing the dephosphorylation of an isopentenyl pyrophosphate (IPP) and/or dimethylallyl diphosphate (DMAPP) to 3-methyl-3-buten-1-ol and/or 3-methyl-2-buten-1-ol, respectively, and the culturing results in the expression of the enzyme, such that the culturing results in the genetically modified host cell producing 3-methyl-3-buten-1-ol and/or 3-methyl-2-buten-1-ol.

In some embodiments of the invention, for the method for producing a 5-carbon alcohol in a genetically modified host cell, the method comprises: (a) introducing a nucleic acid construct encoding an enzyme capable of catalyzing the dephosphorylation of an isopentenyl pyrophosphate (IPP) and/or dimethylallyl diphosphate (DMAPP) to 3-methyl-3-buten-1-ol and/or 3-methyl-2-buten-1-ol, respectively, into a genetically modified host cell; and (b) culturing the genetically modified host cell under a suitable condition such that the enzyme is expressed in the host cell; such that the culturing results in the genetically modified host cell producing 3-methyl-3-buten-1-ol and/or 3-methyl-2-buten-1-ol.

In some embodiments of the invention, the method further comprises the step of recovering the produced 5-carbon alcohol, wherein the recovering step is concurrent or subsequent to the culturing step.

In some embodiments, the host cells are capable of biosynthesis of the 5-carbon alcohol compounds by the coexpression of the appropriate mevalonate or non-mevalonate biosynthetic pathway enzymes to produce IPP and/or DMAPP and the phosphatase, and optionally the reductase, in *E. coli* or yeast. Mevalonate or non-mevalonate biosynthetic pathway enzymes have been thoroughly studied for the production of many medicinally important isoprenoid natural products, and metabolic engineering of the biosynthetic pathway has also been intensively done to improve the production (Ro et al., *Nature* 2006, 440:940; Reiling et al., *Biotechnol. Bioeng.* 2004, 87:200; Martin et al., *Nat. Biotechnol.* 2003, 21:796; which are incorporated in their entireties by reference). Both mevalonate pathway and non-mevalonate pathway have been engineered to produce high titer of isopentenyl diphosphate (IPP) and dimethylallyl diphosphate (DMA PP) (Martin et al., *Nat. Biotechnol.* 2003, 21:796). Instead of terpene cyclases which catalyze the formation of terpenes from diphosphate intermediates, pyrophosphatases are expressed for the production of terpenol and they hydrolyze diphosphate intermediates to the corresponding primary alcohols (Song, *Appl. Biochem. Biotechnol.* 2006, 128:149, which is incorporated in its entirety by reference).

Further Description of the Invention

A. Enzymes, and Constructs Encoding Thereof
  1. Enzymes

The enzymes capable of catalyzing the dephosphorylation of IPP and/or DMAPP include, but are not limited to, a phosphatase, or a homologous enzyme thereof. A homologous enzyme is an enzyme that has a polypeptide sequence that is at least 70%, 75%, 80%, 85%, 90%, 95% or 99% identical to any one of the enzymes described in this specification or in an incorporated reference. The homologous enzyme retains amino acids residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

a) Phosphatases

A first reaction in the de novo pathway catalyzes the dephosphorylation of IPP to 3-methyl-3-butenol and DMAPP to 3-methyl-2-butenol. A suitable phosphatase enzyme has an enzymatic activity for cleaving a pyrophosphate from IPP and/or DMAPP, or cleaving a single phosphate multiple times from IPP and/or DMAPP. A suitable phosphatase enzyme is a broad specificity phosphatase PhoE (YhfR) of a *Bacillus* sp., such as PhoE (YhfR) of *Bacillus stearothermophilus* (such as strains NGB101 and 10; Ridgen et al., *Protein Sci.* 2001, 10:1835-1846, which is incorporated in its entirety by reference), *Bacillus halodurans* (Takami. et al., *Nucleic Acids Res.* (2000) 28:4317-4331, which is incorporated in its entirety by reference) or *Bacillus subtilus* (Kunst et al., *Nature* (1997), 390:249-256; Pearson et al., *J. Bacteriol.* (2000) 182:4121-4123; which are incorporated in their entireties by reference). The amino acid sequences are disclosed in Rigden et al. (*Protein Sci.* (2001) 10:1835-1846), which are incorporated in their entireties by reference. In some embodiments, the suitable phosphatase is about 190 to 210, or about 192 to 209, amino acids in length. A homologous enzyme comprises the conserved amino acid residues and sequences are identified in FIG. 2 and in Rigden et al. (*Protein Sci.* (2001) 10:1835-1846). In some embodiments, a conserved amino acid sequence is RHG; RHGE (SEQ ID NO:1); RHGE(T or S)(SEQ ID NO:2-3);RHGE(T or S)(W or G)N (SEQ ID NO:4-7); or RHGX$_4$N (where X is any amino acid). (SEQ ID NO:8). In some embodiments, a conserved amino acid sequence is RHGEX$_3$NX$_{42}$RX$_{23}$EX$_{56-67}$H (where X is any amino acid) (SEQ ID NO:9). In some embodiments, a conserved amino acid sequence is RHGEX$_3$NX$_5$QG (where X is any amino acid) (SEQ ID NO:10). In some embodiments, a conserved amino acid sequence is RHGX$_4$NX$_{7-9}$DX$_2$LX$_3$G (where X is any amino acid) (SEQ ID NO:11). Further conserved amino acid sequences of the phosphatase are shown in FIG. 1 of Rigden et al. (*Protein Sci.* (2001) 10:1835-1846).

Two exemplary enzyme superfamilies with members able to catalyze the hydrolysis of phosphoester bonds are Nudix (Mildvan et al, *Arch. Biochem. Biophysics* (2005) 433:129) and haloacid dehalogenase (HAD) (Allen and Dunaway-Mariano, *Trends Biochem. Sci.* (2004) 29:495). (see Table 1). Another superfamily able to hydrolyze phosphoester bonds is the cofactor-dependent phosphoglycerate mutase (Rigden et al., *J. Mol. Biol.* (2003) 324:411). Other protein families able to dephosphorylate IPP and DMAPP can be used with the current invention.

TABLE 1

| Superfamily | Organism | Name |
| --- | --- | --- |
| HAD | E. coli | YniC (HAD1) |
| | E. coli | YfbT (HAD2) |
| | E. coli | YieH (HAD3) |
| | E. coli | YihX (HAD4) |
| | E. coli | YjjG (HAD5) |

TABLE 1-continued

| Superfamily | Organism | Name |
| --- | --- | --- |
| | E. coli | YqaB (HAD6) |
| | E. coli | YigB (HAD7) |
| | E. coli | YfrG (HAD8) |
| | E. coli | SerB (HAD0) |
| | E. coli | Gph (HAD10) |
| | E. coli | YcjU (HAD11) |
| | E. coli | YbiV (HAD12) |
| | E. coli | YidA (HAD13) |
| | E. coli | YbhA (HAD14) |
| | E. coli | YbjI (HAD15) |
| | E. coli | YigL (HAD16) |
| | E. coli | OtsB (HAD17) |
| | E. coli | Cof (HAD18) |
| | E. coli | YedP (HAD19) |
| | E. coli | YaeD (HAD20) |
| | E. coli | HisB (HAD21) |
| | E. coli | YrbI (HAD22) |
| Nudix | E. coli | NudA (MutT) |
| | E. coli | NudB |
| | E. coli | NudC |
| | E. coli | NudD (Gmm) |
| | E. coli | NudE |
| | E. coli | NudF |
| | E. coli | NudG |
| | E. coli | NudH (RppH) |
| | E. coli | NudI (YfaO) |
| | E. coli | NudJ (YmfB) |
| | E. coli | NudK (YffH) |
| | E. coli | NudL (YeaB) |

In some embodiments suitable phosphatases are members of the Nudix hydrolase superfamily from, but not limited to, *Escherichia* sp., *Bacillus* sp., *Pseudomonas* sp., *Lactococcus* sp., *Caulobacter* sp., *Agrobacterium* sp., *Synechocvtis* sp., *Streptomyces* sp., *Saccharomyces* sp., human, and mouse. An exemplar nucleic acid sequence of Nudix hydrolase family is found at GenBank accession No. NP_009669. In some embodiments the Nudix superfamily recognizes the general substrate motif nucleoside diphosphate linked to another moiety. In some embodiments the Nudix enzymes have a conserved 23-amino acid catalytic motif (Nudix box), consisting of the consensus sequence GX$_5$EX$_5$[UA]XREX$_2$EEXGU, (SEQ ID NOs:12-13),where U is an aliphatic, hydrophobic residue and X is any amino acid (McLennan, A. G., *Cell Mol. Life. Sci.* (2006) 63:123). There also exist individuals in the superfamily with slightly altered consensus residues. Examples of Nudix hydrolases from *E. coli* are listed in Table 1, but are not meant to limit the scope of the present invention.

In some embodiments suitable phosphatases are members of the halocid dehalogenase (HAD) superfamily from, but not limited to, *Escherichia* sp., *Bacillus* sp., *Pseudomonas* sp., *Lactococcus* sp., *Caulobacter* sp., *Agrobacterium* sp., *Synechocytis* sp., *Streptomyces* sp., *Saccharomyces* sp., human, and mouse. HADs have 10-30% sequence similarity can be identified from three short conserved sequence motifs that include a conserved aspartic acid, a serine/threonine, a lysine, and a nucleophile, such as an aspartic acid or serine. The consensus sequence for the amino acid sequence motifs are disclosed in FIG. 2 of Koonin and Tatusov, *J. Mol. Biol.* (1994) 244:125; which are incorporated in their entireties by reference) and Supplementary FIG. 1 of Kuznetsova, et al., (*J. Biol. Chem.* (2006) 281:36149; which is incorporated in their entireties by reference). Examples of HADs from *E. coli* are listed in Table 1, but are not meant to limit the scope of the present invention.

b) Reductases

A second reaction, optionally, in the pathway catalyzes the reduction of the α,β-unsaturated bond in 3-methyl-2-butenol, converting it to isopentanol (3-methyl-butanol). Prior to the present invention a reductase capable of reducing α,β-unsaturated alcohols had not been identified.

The enzymes capable of catalyzing the reduction of 3-methyl-2-butenol to 3-methyl-butantol include, but are not limited to, a reductase, or a homologous enzyme thereof. A homologous enzyme is an enzyme that has a polypeptide sequence that is at least 70%, 75%, 80%, 85%, 90%, 95% or 99% identical to any one of the enzymes described in this specification or in an incorporated reference. The homologous enzyme retains amino acids residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof

TABLE 2

| Family | Organism | Name | Gene Locus |
|---|---|---|---|
| Old yellow enzyme | S. cerevisiae | OYE2 | YHR179w |
|  | S. cerevisiae | OYE3 | YPL171c |
| Aldo-keto reductase | S. cerevisiae | GCY1 | YOR120w |
|  | S. cerevisiae | YPR1 | YDR368w |
|  | S. cerevisiae | ARA1 | YBR149w |
|  | S. cerevisiae | GRE3 | YHR104w |
|  | S. cerevisiae | Uncharacterized | YDL124w |
|  | S. cerevisiae | Uncharacterized | YJR096w |
| Short-chain dehydrogenase | S. cerevisiae | Uncharacterized | YIR036c |
|  | S. cerevisiae | Uncharacterized | YMR226c |
| Dihydroflavonol reductase | S. cerevisiae | GRE2 | YOL151w |
|  | S. cerevisiae | Uncharacterized | YGL157w |
|  | S. cerevisiae | Uncharacterized | YDR541c |
|  | S. cerevisiae | Uncharacterized | YGL039w |
| Zn-dependent deydrogenase | S. cerevisiae | BDH1 | YAL060w |
|  | S. cerevisiae | XYL2 | YLR070c |
| Hydroxy-acid dehydrogenase | S. cerevisiae | Uncharacterized | YGL185c |
|  | S. cerevisiae | GOR1 | YNL274c |
|  | S. cerevisiae | Uncharacterized | YPL113c |
| Aryl-alcohol dehydrogenase | S. cerevisiae | AAD3 | YCR107w |
|  | S. cerevisiae | AAD14 | YNL331c |
| Unknown | S. cerevisiae | FDH2 | YPL275w |

Suitable reductases are described in Ward et al. (*Enzyme Microb. Technol.* 1990, 12:482-493) and Rodríguez et al. (*J. Am. Chem. Soc.* 2001, 123:1547-1555), which are incorporated in their entireties by reference. A suitable reductase is any enzyme capable of hydrogenating the double bond of 3-methyl-2-buten-1-ol to form 3-methyl-butan-1-ol. A particular suitable reductase is an enzyme that has enoyl reductase activity. Suitable enzymes which may be used to hydrogenate the double bond of 3-methyl-2-buten-1-ol include, but is not limited to, a yeast oxidoreductase (Ward et al., *Enzyme Microb. Technol.* 1990, 12:482-493). Such an enzyme is the fatty acid synthase of *Saccharomyces cerevisiae*, which contains a functional domain with enoyl reductase activity. Other suitable reductases are a *Torulaspora delbrueckii* fatty acid synthase and *Kluyveromyces lactis* fatty acid synthase (King et al., *Yeast* 16:499-506 (2000), which is incorporated in its entirety by reference), and *E. coli* fatty acid synthase.

In some embodiments a reductase suitable for use in this invention is an enzyme that has enoyl reductase activity. Such an enzyme is the fatty acid synthase of *Saccharomyces cerevisiae.*, which contains a functional domain with enoyl reductase activity. Other suitable enzymes are the fatty acid synthase of *Torulaspora delbrueckii* and *Kluyveromyces lactis* (King et al., *Yeast* (2000) 16:499-506, which is incorporated in its entirety by reference).

In some embodiments the reductases are members of the Old Yellow Enzyme (OYE) family of flavoproteins from, but not limited to, *Saccharomyces* sp., *Escherchia* sp., *Eubacterium* sp., *Pseudomonas* sp., *Kluyveromyces* sp., *Candida* sp., *Gluconobacter* sp., *Bacillus* sp., and *Zymomonas* sp. Members of the OYE family use flavin mononucleotide (FMN) as a co-factor and share a conserved region of residues with the consensus sequence SNXRTDEYGG(S OR T) where X is any amino acid residue(SEQ ID Nos14-15). OYEs are characterized as single-domain proteins with an approximate size of 45 kDa with an α/β barrel fold. Structures and descriptions of OYEs are described in Williams and Bruce, *Microbiology* (2002) 148:1607; which is incorporated by reference in its entirety). An exemplar nucleic acid sequence for oye family members is located at Gene Bank accession No. NP_012049.

Figure 6:
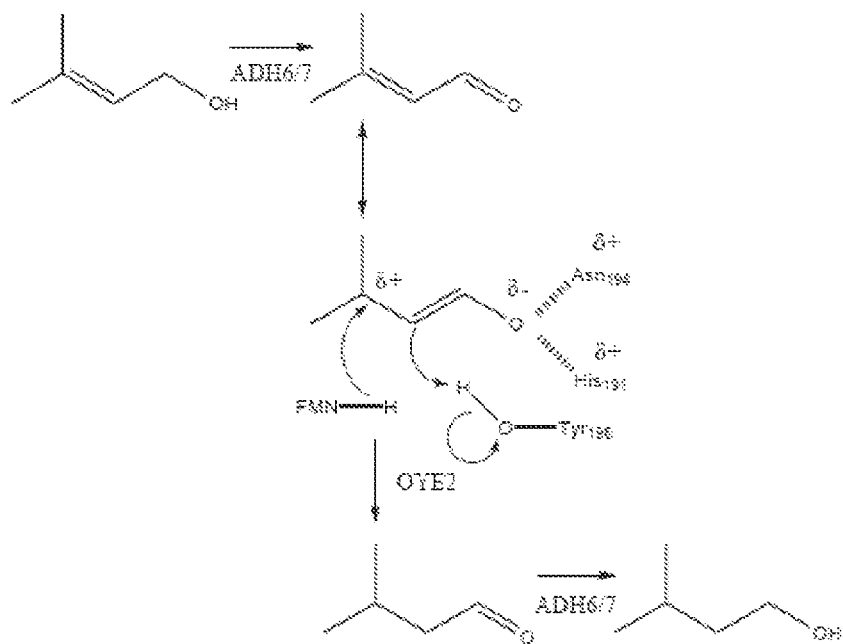
FIG. 6 shows a hypothetical mechanism for the reduction of 3-methyl-2-butenol to isopentanol by OYE.

Without limitation to a particular theory or mode of action a hypothetical mechanism by which OYE proteins might be involved in the reduction of 3-methyl-2-butenol is provided (FIG. 6). We propose that yeast alcohol dehydrogenase (ADH) first converts the alkenol to 3-methyl-2-butenal before the carbon-carbon double bond is reduced by OYE2. The aldehyde intermediate is then reduced to isopentanol.

c) Alcohol Dehydrogenases

In some embodiments enzymes capable of catalyzing the interconversion of branched-C5 alcohols to branched-C5 aldehydes include, but are not limited to, a dehydrogenase, or a homologous enzyme thereof are employed. A homologous enzyme is an enzyme that has a polypeptide sequence that is at least 70%, 75%, 80%, 85%, 90%, 95% or 99% identical to any one of the enzymes described in this specification or in an incorporated reference. The homologous enzyme retains amino acids residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

Suitable alcohol dehydrogenases (ADHs) that can interconvert branched-C5 alcohols to branched-C5 aldehydes are members of the zinc-dependent medium-chain dehydrogenase/reductase (MDR) family. The zinc-dependent ADHs have the consensus sequence: GHEX$_2$GX$_5$(G,A)X$_2$(I,V,A,C,S) (SEQ ID Nos:16-25)(Larry, et al., *Eur. J. Biochem.* (2002) 269:5738, which is incorporated by reference in its entirety), and include, but are not limited to, ADH1, ADH2, ADH3, ADH5, SFA1, SOR1, YDL246c, XYL2, BDH1, YAL061w, and YCR105w.

Yeast ADHs demonstrate promiscuous oxidase and reductase activities toward a wide variety of substrates (Dickinson and Dack, *Chem-Biol. Inter.* (2001) 130-132:417). ADH6 and ADH7 are members of the cinnamyl alcohol dehydrogenase family. In some embodiments the alcohol dehydrogenase are members of the cinnamyl alcohol dehydrogenase family. In some embodiments the alocohol dehydrogenase is ADH6 and ADH7.

2. Constructs

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521: 719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host cell simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the drt are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the Lad repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter. (See deBoer et al. (1983) *Proc. Natl. Acad. Sci. USA,* 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBRIMCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hvg genes.

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain an excess carbon source, such as a sugar (e.g., glucose) when an intermediate is not introduced. In this way, cellular production of acetyl-CoA, a starting material for IPP and DMAPP synthesis is ensured. When added, the intermediate is present in an excess amount in the culture medium.

As the host cell grows and/or multiplies, expression of the enzymes necessary for producing the 5-carbon alcohol is effected. Once expressed, the enzymes catalyze the steps necessary for carrying out the steps of IPP and/or DMAPP acid production and the 5-carbon alcohol production, i.e., converting IPP and/or DMAPP into 5-carbon alcohol is 3-methyl-2-buten-1-ol, 3-methyl-3-buten-1-ol and/or 3-methyl-butan-1-ol. If an intermediate has been introduced, the expressed enzymes catalyze those steps necessary to convert the intermediate into the respective IPP and/or DMAPP. Any means for recovering the 5-carbon alcohol from the host cell may be used. For example, the host cell may be harvested and subjected to hypotonic conditions, thereby lysing the cells. The lysate may then be centrifuged and the supernatant subjected to high performance liquid chromatography (HPLC) or gas chromatography (GC).

B. Host Cells

The host cells of the present invention are genetically modified in that heterologous nucleic acid have been introduced into the host cells, and as such the genetically modified host cells do not occur in nature. The suitable host cell is one capable of expressing a nucleic acid construct encoding an enzyme capable of catalyzing the dephosphorylation of IPP and/or DMAPP, and optionally an enzyme capable of reducing 3-methyl-2-buten-1-ol into 3-methyl-butan-1-ol. Such enzymes are described herein. In some embodiments, the host cell naturally produces IPP and/or DMAPP, and optionally may comprises heterologous nucleic acid constructs capable of expressing one or more genes for producing IPP and/or DMAPP. The gene may be heterogous to the host cell or the gene may be native to the host cell but is operatively linked to a heterologous promoter and one or more control regions which result in a higher expression of the gene in the host cell. In other embodiments, the host cell does not naturally produce IPP and/or DMAPP, and comprises heterologous nucleic acid constructs capable of expressing one or more genes for producing IPP and/or DMAPP.

The enzyme capable of catalyzing the dephosphorylation of IPP and/or DMAPP can be native or heterologous to the host cell. Similarly, the enzyme capable of catalyzing the reduction of 3-methyl-2-buten-1-ol into 3-methyl-butan-1-ol can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

The host cells produce the IPP and/or DMAPP that is dephosphorylated into 3-methyl-3-buten-1-ol and/or 3-methyl-2-buten-1-ol, respectively. The host cell comprises the genes encoding enzymes in the pathway from which the IPP and/or DMAPP are synthesized from acetyl-CoA. Optionally, the host cell may comprise a gene encoding the enzyme that reduces 3-methyl-2-buten-1-ol into 3-methyl-butan-1-ol. These genes can either be native to the host cell or are heterologous to the host cell and introduced all or in part into the host cell either by integration into the host cell chromosome(s) or an expression vector, or both.

The host cells may comprise systems for synthesizing IPP and/or DMAPP. Such systems are taught in U.S. Pat. Nos. 7,172,886 and 7,183,089, and U.S. Pat. Application Pub. No. 2003/0148479, 2006/0079476, 2007/0077616, 2007/0092931, and 2007/0099261, which are incorporated in their entireties by reference. Such methods include producing an IPP and/or DMAPP in a genetically modified host cell, such as *E. coli*.

The host cells may express pyrophosphases which hydrolyze the isoprenyl diphosphate intermediates to the corresponding primary alcohols (Song, *Appl. Biochem. Biotechnol.* 2006, 128:149, which is incorporated in its entirety by reference). The host cells may be knocked out for or lack expression of any terpene cyclases which catalyze the formation of terpenes from diphosphate intermediates.

IPP and DMAPP are generated in vivo via either the mevalonate pathway or the non-mevalonate pathway (also known as the DXP pathway), which is described in Reiling et al., *Biotechnol. Bioeng.* 87(2):200-212 (2004), which is incorporated in its entirety by reference.

In some embodiments, a host cell may naturally be capable of hydrogenating the double bond of 3-methyl-2-buten-1-ol. Such a host cell may not be modified in order to be able to produce 3-methyl-butan-1-ol from 3-methyl-2-buten-1-ol, or the gene encoding the enzyme for catalyzing this reaction can be modified so that expression of the enzyme is increased. A host cell that may not require modification is *Saccharomyces cerevisiae*. Gramatica et al. (*Experientia* 38, 1982) have shown that *S. cerevisiae* is capable of reducing geraniol to R-(+)-citronellol. Gramatica et al. (*J. Org. Chem.* 50, 1985) have shown that *S. cerevisiae* is capable of hydrogenating the double bonds in α- or β-methyl-α,β-unsaturated aldehydes (including alcohols and acetals).

Figure 3:
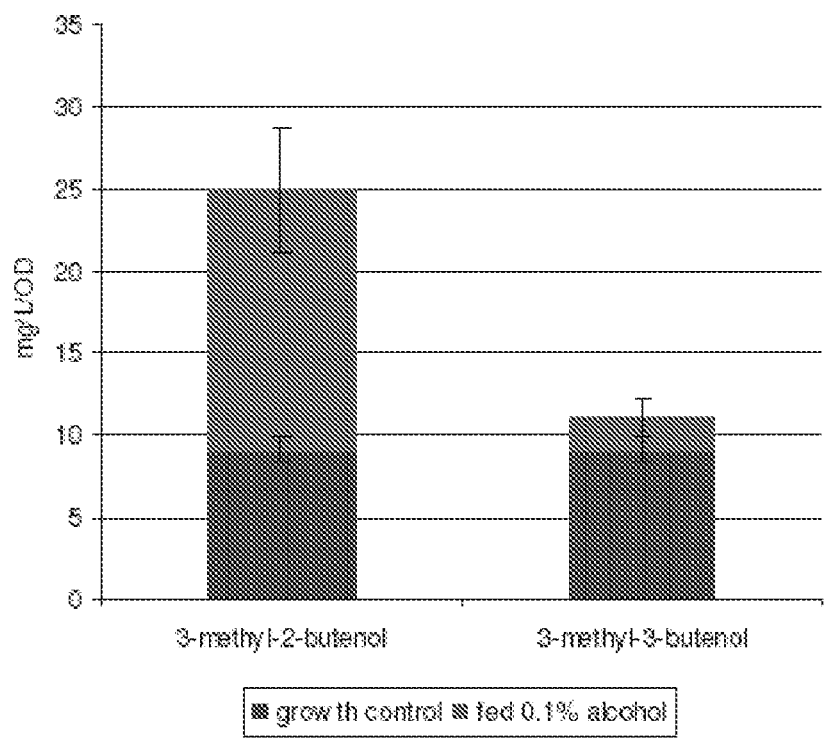
FIG. 3 shows the relative transformation of 3-methyl-2-butenol and 3-methyl-3-butenol to isopentanol by *Saccharomyces cerevisiae*. The y-axis is milligrams of isopentanol/L/O.D. Dark shaded bars represent the production of isopentanol by *S. cerevisiae* in the absence of added alcohol substrate. Light shaded bars represent transformation of substrate alcohol by *S. cerevisiae* into isopentanol.

It is now shown in the present invention that yeast can catalyze the conversion of 3-methyl-2-butenol to isopentanol (see FIG. 3).

Any prokaryotic or eukaryotic host cell may be used in the present method so long as it remains viable after being transformed with a sequence of nucleic acids. Generally, although not necessarily, the host microorganism is bacterial. Examples of bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla, Synechococcus*, and *Paracoccus* taxonomical classes. In some embodiments, the microorganism is a cyanobacteria. In some embodiments the bacterial host is *Synechocystis* sp. Preferably, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host cell's own metabolic processes and those processes involved with the mevalonate pathway.

Suitable eukaryotic cells include, but are not limited to, algal, fungal, insect or mammalian cells. In some embodiments, suitable fungal cells are yeast cells, such as yeast cells of the *Saccharomyces* genus. In some embodiments the eukaryotic cell is a green algae. In some embodiments the eukaryotic cell is *Chlamydomonas reinhardtii, Scenedesmus obliquus, Chlorella vulgaris* or *Dunaliella salina*.

The host cell can further be modified to comprise endogenous solvent efflux system such as AcrAB-TolC (Ramos et al., *Annu Rev Microbiol* 2002, 56:743, which is incorporated in its entirety by reference) to pump the 5-carbon alcohol produced by the host cell out of the cell. When the host cell is capable of pumping the produced 5-carbon alcohol out of the cell, the 5-carbon alcohol can be recovered by removal of the supernatant in which the host cell is being cultured.

The toxicity of the branched-C5 alcohols will not be problematic for the viability of host cells during fermentation. The minimum inhibitory. concentration (MIC) of the alcohols is approximately 1% (w/v) for *E. coli*. The branched-C5 alcohols begin to phase separate at this concentration from the growth medium.

C. Isolation of 5-Carbon Alcohols Produced

The present invention provides for an isolated 5-carbon alcohol produced from the method of the present invention. Isolating the 5-carbon alcohol involves the separating at least part or all of the host cells, and parts thereof, from which the 5-carbon alcohol was produced, from the isolated 5-carbon alcohol. The isolated 5-carbon alcohol may be free or essentially free of impurities formed from at least part or all of the host cells, and parts thereof. The isolated 5-carbon alcohol is essentially free of these impurities when the amount and properties of the impurities do not interfere in the use of the 5-carbon alcohol as a fuel, such as a fuel in a combustion reaction. These host cells are specifically cells that do not in nature produce the 5-carbon alcohol. The impurities are no more than 5%, 1%, 0.5%, 0.1%, 0.05%, or 0.01% by weight of a composition comprising one or more of the 5-carbon alcohols.

The present invention also provides for a combustible composition comprising an isolated 5-carbon alcohol and cellular components, wherein the cellular components do not substantially interfere in the combustion of the composition. The cellular components include whole cells or parts thereof. The cellular components are derived from host cells which produced the 5-carbon alcohol was derived.

The 5-carbon alcohol of the present invention are useful as fuels as chemical source of energy that can be used as an alternative to petroleum derived fuels, ethanol and the like.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLES

The following examples are provided by way of illustration only and not by way of limitation. Those of skill in the art will readily recognize a variety of non-critical parameters that could be changed or modified to yield essentially similar results.

All solvents, standards, and antibiotics (e.g. tetracycline, chloramphenicol, kanamycin, carbenicillin) were purchased from Sigma-Aldrich (St. Louis, Mo.) unless otherwise indicated. 3-methyl-2-butenol and 3-methyl-butanol were purchased from Tokyo Chemical Industry (Portland, Oreg.). Phusion polymerase and all restriction enzymes were purchased from New England Biolabs (Ipswich, Mass.).SuperScriptIII Reverse Transcriptase was purchased from Invitrogen (Carlsbad, Calif.). IPTG was obtained from EM Sciences (Gibbstown, N.J.).

Example 1

Production of 3-methyl-2-buten-1-ol and 3-methyl-3-buten-1-ol in a Host Cell

The pMevT plasmid (containing the genes for synthesizing mevalonate from acetyl-CoA) and pMBI (containing the genes for synthesizing IPP and DMAPP from mevalonate) are introduced into *E. coli* DH10B, which then is capable of expressing IPP and DMAPP. The method for constructing the pMevT plasmid, and nucleotide sequence, are taught in U.S. Pat. No. 7,183,089, which is incorporated in its entirety by reference. The method for constructing the pMBI plasmid is taught in Martin et al. (*Nature Biotechnol.* 21:796-802 (2003)), which is incorporated in its entirety by reference.

Primers can be designed to PCR *Bacillus subtilus* phosphatase PhoE (YhfR) from *Bacillus subtilus* genomic DNA and cloned into a suitable *E. coli* expression vector. The resultant plasmid is introduced into an *E. coli* host cell also containing the pMevT and pMBI plasmids. The resulting transformant is cultured in a suitable medium, such as Luria broth (LB) medium at 37° C. with the appropriate antibiotics to maintain the plasmids. The enzymes are induced using the appropriate inducers, such as IPTG or propionate, and incubated at 30° C. for 3-7 days. The induction of the enzymes results in the production of 3-methyl-2-buten-1-ol and/or 3-methyl-3-buten-1-ol from DMAPP and/or IPP, respectively.

The 3-methyl-2-buten-1-ol and/or 3-methyl-3-buten-1-ol can be purified and analyzed using a gas chromatography-mass spectrometer (GC-MS).

Example 2

Production of 3-methyl-butan-1-ol in a Host Cell

Primers can be designed to PCR *Saccharomyces cerevisiae* fatty acid synthase from *Saccharomyces cerevisiae* genomic DNA and cloned into a suitable *E. coli* expression vector. The resultant plasmid is introduced into an *E. coli* host cell also containing the pMevT and pMBI plasmids, and a plasmid expressing *Bacillus subtilis* phosphatase YhfR. The resulting transformant is cultured in a suitable medium, such as Luria broth (LB) medium at 37° C. with the appropriate antibiotics to maintain the plasmids. The enzymes are induced using the appropriate inducers, such as IPTG or propionate, and incubated at 30° C. for 3-7 days. The induction of the enzymes results in the production of 3-methyl-butan-1-ol. The 3-methyl-butan-1-ol can be purified and analyzed using a GC-MS.

Example 3

In Vivo Reduction of 3-methyl-2-butenol or 3-methyl-3-butenol to 3-methyl-butanol To test the capability of yeast to catalyze the conversion of 3-methyl-2-butenol to isopentanol, 5 ml. of YPD medium with 2% glycerol, in a 100 ml culture tube, was inoculated with an overnight culture of freshly plated *S. cerevisiae* BY4741 cells to achieve a final absorbance of 0.5 at 600 nm ($A_{600}$). The cultures were grown at 30° C. at 200 r.p.m. After 48 hours, either 3-methyl-2-butenol or 3-methyl-3-butenol (1 g/l) was added to the culture.

Cultures were sampled after addition of 3-methyl-2-butenol or 3-methyl-3-butenol and grown for an additional 2 days. The samples were collected by pelleting 1 ml of culture, and adding 150 μl of the supernatant to 750 μl of the extraction solvent (80:20 chloroform:methanol spiked with 50 mg l$^{-1}$ of butanol internal standard). The samples were vortexed for 15 minutes and centrifuged for 2 minutes at 5000 r.c.f. 450 μl of the organic layer was removed from each sample and transferred to a clean GC vial for analysis. The GC-MS data were collected in full-scan mode (m/z 50-300) using a Tr-Wax column (0.25 mm×30 m, 0.25 μm film thickness; Thermo Electron) on a PolarisQ GC-MS with TriPlusautosampler (Thermo Electron). The carrier flow was 1.2 ml min$^{-1}$, and the inlet temperature was set to 200° C. The oven program was as follows: 40° C. (1.20 min hold), 40-130° C. (25° C. min$^{-1}$), 130-220° C. (35° C. min$^{-1}$). The solvent delay was set at 3.40 min. Samples were normalized using the butanol internal standard and quantified using authentic standards.

Yeast grown in the presence of 3-methyl-2-butenol produced significantly more isopentanol than yeast grown in the absence of 3-methyl-2-butenol (FIG. 3, left hand column, light bar compared to dark bar) or those grown in the presence of 3-methyl-3-butenol (FIG. 3, left hand column relative to right hand column).

Example 4

Construction of Yeast Reductase Library

The yeast reductase genes were amplified from a *S. cerevisiae* BY4742 cDNA library and inserted into pESC-leu with the appropriate restriction enzymes using standard protocols. The cDNA library was made following Invitrogen's suggested method for SuperScript III Reverse Transcriptase, the incubation was extended from 1 hour to 3 hours in Step 5 of the manufacturer's protocol.

The primers used to amplify YHR179w were 5'-AAC CGT CGA CAT GCC ATT TGT TAA GGA CTT TAA G-3' (SEQ ID NO:26) and 5'-TAA CGC TAG CTT AAT TTT TGT CCC AAC CGA GTT TTA GAG C-3' (SEQ ID NO:27), and the gene was inserted into the NheI-SalI sites of pESC-leu. The primers used to amplify YPL171c were 5'-AACCGTCGA-CATGCCATTTGTAAAAGGTTTTGAGC-3' (SEQ ID NO:28) and 5'-TAACGCTAGCTCAGTTCTTGTTCCAAC-CTAAATCTAC-3' (SEQ ID NO:29), and the gene was inserted into the NheI-SalI sites of pESC-leu. The primers used to amplify YOR120w were 5'-AACCGGATCCATGC-CTGCTACTTTACATGATTC-3' (SEQ ID NO:30) and 5'-TAACCTCGAGTTACTTGAATACTTCGAAAGGAG-3' (SEQ ID NO:31), and the gene was inserted into the BamHI-XhoI sites of pESC-leu. The primers used to amplify YDR368w were 5'-AACCGTCGACATGCCTGCTACGT-TAAAGAA-3' (SEQ ID NO:32) and 5'-TAACCTCGAGT-CATTGGAAAATTGGGAAG-3' (SEQ ID NO:33), and the gene was inserted into the SalI-XhoI sites of pESC-leu. The primers used to amplify YBR149w were 5'-AACCGGATC-CATGTCTTCTTCAGTAGCCTC-3' (SEQ ID NO:34) and 5'-TAACGCTAGCTTAATACTTTAAATTGTCCAAG-3' (SEQ ID NO:35), and the gene was inserted into the BamHI-NheI sites of pESC-leu. The primers used to amplify YHR104w were 5'-AACCGGATCCATGTCTTCACTGGT-TACTCTTA-3' (SEQ ID NO:36) and 5'-TAACCTCGAGT-CAGGCAAAAGTGGGGAAT-3' (SEQ ID NO:37), and the gene was inserted into the BamHI-XhoI sites of pESC-leu. The primers used to amplify YDL124w were 5'-AACCG-GATCCATGTCATTTCACCAACAGTTC-3' (SEQ ID NO:38) and 5'-TAACCTCGAGTTATACTTTTTGAG-CAGCG-3' (SEQ ID NO:39), and the gene was inserted into the BamHI-XhoI sites of pESC-leu. The primers used to amplify YJR096w were 5'-AACCGGATCCATGGTTC-CTAAGTTTTACAAAC-3' (SEQ ID NO:40) and 5'-TAAC-CTCGAGTTATGGCGCGTCTGTGCATTC-3' (SEQ ID NO:41), and the gene was inserted into the BamHI-XhoI sites of pESC-leu. The primers used to amplify YIR036c were 5'-AACCGGATCCATGGGCAAGGTTATTTTGATTA-3' (SEQ ID NO:42) and 5'-TAACGCTAGCCTAGCCCTG-CACCGGCCCCAGTC-3' (SEQ ID NO:43), and the gene was inserted into the BamHI-NheI sites of pESC-leu. The primers used to amplify YMR226c were 5'-AACCGGATC-CATGTCCCAAGGTAGAAAAGCTG-3' (SEQ ID NO:44) and 5'-TAACGCTAGCTTATCCACGGAAGATAT-GATGAGGT-3' (SEQ ID NO:45), and the gene was inserted into the BamHI-NheI sites of pESC-leu. The primers used to amplify YOL151w were 5'-AACCGGATCCATGT-CAGTTTTCGTTTCAGGTG-3' (SEQ ID NO: 46) and 5'-TAACCTCGAGTTATATTCTGCCCT-CAAATTTTAAAA-3' (SEQ ID NO: 47), and the gene was inserted into the BamHI-XhoI sites of pESC-leu. The primers used to amplify YGL157w were 5'-AACCGGATCCATGAC-TACTGATACCACTGTTTTC -3' (SEQ ID NO:48) and 5'-TAACCTCGAGTTAGGCTTCATTTTGAAC-3' (SEQ ID NO:49), and the gene was inserted into the BamHI-XhoI sites of pESC-leu. The primers used to amplify YDR541c were 5'-AACCGGATCCATGTCTAATACAGTTCTAG -3' (SEQ ID NO:50) and 5'-AACCGGATCCTCATAATCTGTTCTC-CTTCTTC-3' (SEQ ID NO:51), and the gene was inserted into the BamHI-XhoI sites of pESC-leu. The primers used to amplify YGL039w were 5'-AACCGTCGACATGACTACT-GAAAAAACCGTTG-3' (SEQ ID NO:52) and 5'-TAACGCTAGCTTAGCTTT-TACTTTGAACTTCTAGTAATTGCG-3' (SEQ ID NO:53), and the gene was inserted into the NheI-SalI sites of pESC-leu. The primers used to amplify YAL060w were 5'-AACCG-GATCCATGAGAGCTTTGGCATATTTC-3' (SEQ ID NO:54) and 5'-TAACCTCGAGTTACTTCATTTCAC-CGTGA-3' (SEQ ID NO:55), and the gene was inserted into the BamHI-XhoI sites of pESC-leu. The primers used to amplify YLR070c were 5'-AACCGGATCCATGACTGACT-TAACTACACA-3' (SEQ ID NO:56) and 5'-TAACCTC-GAGTCATTCCGGGCCCTCAATGATC-3' (SEQ ID NO:

57), and the gene was inserted into the BamHI-XhoI sites of pESC-leu. The primers used to amplify YGL185c were 5'-AACCGGATCCATGTGCGATTCTCCTGCA-3' (SEQ ID NO:58) and 5-TAACCTCGAGTCAAACTACACGG-GAGAAATGCT-3' (SEQ ID NO:59), and the gene was inserted into the BamHI-XhoI sites of pESC-leu. The primers used to amplify YNL274c were 5'-AACCGGATCCATGAG-TAAGAAACCAATTGTTTTG-3' (SEQ ID NO:60) and 5'-TAACCTCGAGTCAAACTAATGGCTTAGATTC-3' (SEQ ID NO:61), and the gene was inserted into the BamHI-XhoI sites of pESC-leu. The primers used to amplify YPL113c were 5'-AACCGGATCCATGATTACTTCAAT-TGACATAGCAG-3' (SEQ ID NO:62) and 5'-TAACGCTAGCTCAGTTGAGCACATACT-TACCATCAC-3' (SEQ ID NO:63), and the gene was inserted into the BamHI-NheI sites of pESC-leu. The primers used to amplify YCR107w were 5'-AACCGGATCCATGAT-TGGGTCCGCGTCCGA-3' (SEQ ID NO:64) and 5'-TAAC-CTCGAGCTAAACATTATTCGTACC-3' (SEQ ID NO:65), and the gene was inserted into the BamHI-XhoI sites of pESC-leu. The primers used to amplify YNL331c were 5'-AACCGGATCCATGACTGACTTGTTTAAACCTC-3' (SEQ ID NO:66) and 5'-TAACCTCGAGCTAATTGT-CAAAAGCTATCCTG-3' (SEQ ID NO:67), and the gene was inserted into the BamHI-XhoI sites of pESC-leu. The primers used to amplify YPL275w were 5'-AACCGGATC-CATGGTGGTCATCAATAAGCAATTA-3' (SEQ ID NO:68) and 5'-TAACCTCGAGTTATTTCTTCTGTCCAT-AAGCTCTGG-3' (SEQ ID NO:69), and the gene was inserted into the BamHI-XhoI sites of pESC-leu.

Example 5

Screening of Candidates for Reduction of 3-methyl-2-butenol to 3-methyl-butanol

To identify enzymes with the capability to catalyze the reduction 3-methyl-2-butenol to 3-methyl-butanol the following assay system was employed. 5 ml of synthetic defined medium lacking leucine with 1.8% galactose and 0.2% glucose was inoculated with an overnight culture of *S. cerevisiae* BY4741 freshly transformed with a vector (pESC) expressing a reductase candidate gene to achieve a final absorbance of 0.5 at 600 nm ($A_{600}$). The cultures were grown at 30° C. at 200 r.p.m. After 48 hours, 3-methyl-2-butenol (1 g/l) was added to the culture.

Cultures were sampled for isopentanol production after addition of 3-methyl-2-butenol as described in Example 3.

Figure 4:
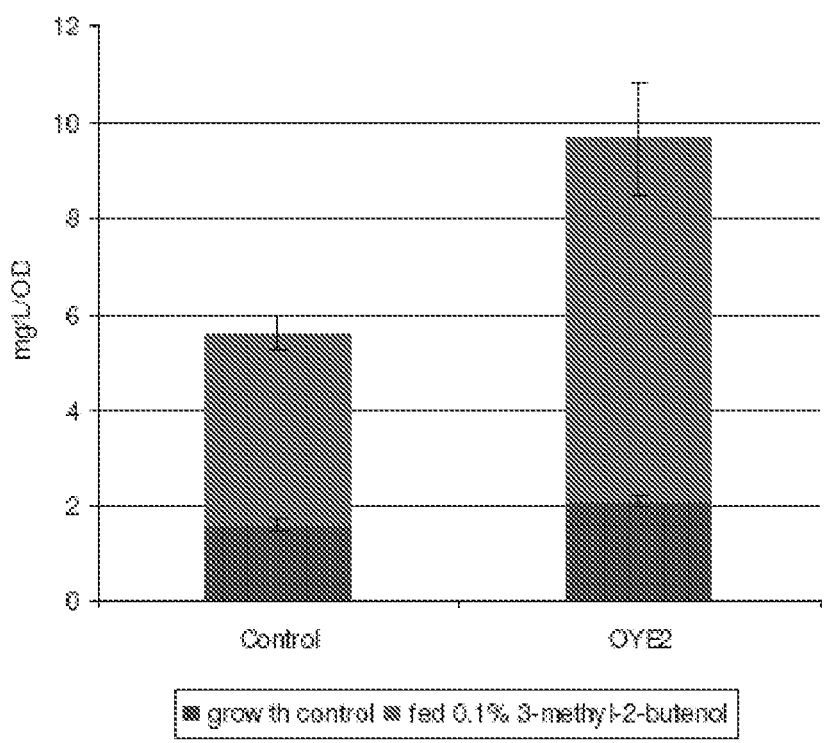
FIG. 4 shows the relative transformation of 3-methyl-2-butenol to isopentanol by *Saccharomyces cerevisiae* with or without over-expressing oye2. The y-axis is milligrams of isopentanol/L/O.D. Dark shaded bars represent the production of isopentanol by *S. cerevisiae* in the absence of added alcohol substrate. Light shaded bars represent transformation of substrate alcohol by *S. cerevisiae* into isopentanol.
Figure 5:
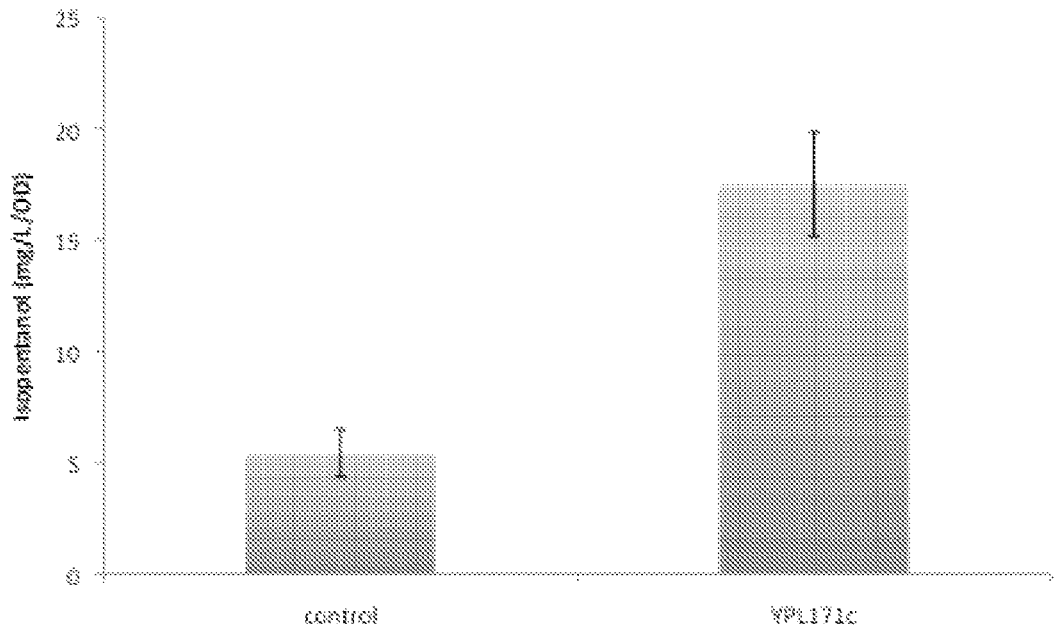
FIG. 5 shows the relative transformation of 3-methyl-2-butenol to isopentanol by *Saccharomyces cerevisiae* with or without over-expressing oye3 (YPL171c) shows a hypothetical mechanism for the reduction of 3-methyl-2-butenol to isopentanol by OYE2.

Yeast genetically modified to over-express either OYE2 or OYE3 showed a significant increase in isopentanol production relative to controls (FIGS. 4 and 5).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for producing a 5-carbon alcohol in a genetically modified host cell, the method comprising: culturing a genetically modified host cell under a suitable condition, wherein the genetically modified host cell is transformed with a first nucleic acid construct encoding a first enzyme capable of catalyzing the dephosphorylation of an isopentenyl pyrophosphate (IPP) or dimethylallyl diphosphate (DMAPP), such that the culturing results in the genetically modified host cell producing a 5-carbon alcohol, wherein the 5-carbon alcohol is 3-methyl-2-buten-1-ol, or 3-methyl-3-buten-1-ol.

2. The method of claim 1, further comprising the step of: (b) recovering the produced 5-carbon alcohol, wherein the recovering step is concurrent or subsequent to the culturing step.

3. The method of claim 1, wherein the first enzyme is *Bacillus* sp. YhfR, having the amino acid sequence of SEQ ID NO:70.

4. The method of claim 1, wherein the genetically modified host cell is further transformed with a second nucleic acid construct encoding a second enzyme capable of reducing a 3-methyl-2-buten-1-ol, such that the culturing results in the genetically modified host cell producing 3-methyl-butan-1-ol, wherein the first nucleic acid construct and the second nucleic acid construct reside on the same nucleic acid or two separate nucleic acids.

5. The method of claim 4, wherein the second enzyme is a reductase.

6. The method of claim 5, wherein the reductase is an *Escherichia coli*, *Saccharomyces cerevisiae*, *Torulaspora delbrueckii*, or *Kluyveromyces lactis* fatty acid synthase.

7. The method of claim 5, wherein the reductase is an OYE family member.

8. The method of claim 7, wherein the reductase is a *Saccharomyces* sp. OYE family member.

9. The method of claim 7, wherein the OYE family member is OYE2.

10. The method of claim 7, wherein the OYE family member is OYE3.

11. The method of claim 4, further comprising the step of: (b) recovering the produced 3-methyl-butan-1-ol, wherein the recovering step is concurrent or subsequent to the culturing step.

12. The method of claim 1, wherein the 5-carbon alcohol is 3-methyl-2-buten-1-ol.

13. The method of claim 1, wherein the 5-carbon alcohol is 3-methyl-3-buten-1-ol.

14. The method of claim 1, wherein the host cell is a eubacteria.

15. The method of claim 14, wherein the host cell is one selected from the *Escherichia, Enterobacter, Azotobacter, Erwinia, Bacillus, Pseudomonas, Klebsielia, Proteus, Salmonella, Serratia, Shigella, Rhizobia, Vitreoscilla, Synechococcus, Synechocystis*, and *Paracoccus* taxonomical classes.

16. The method of claim 14, wherein the host cell is *Escherichia coli*.

17. The method of claim 1, wherein the host cell is an algal, fungal, insect, or an isolated mammalian cell line.

18. The method of claim 17, wherein the host cell is a yeast.

19. The method of claim 18, wherein the host cell is *Saccharomyces cerevisae*.

20. A genetically modified host cell transformed with a first nucleic acid construct encoding a first enzyme capable of catalyzing the dephosphorylation of an isopentenyl pyrophosphate (IPP) or dimethylallyl diphosphate (DMAPP), which under a suitable condition produces 3-methyl-2-buten-1-ol, or 3-methyl-3-buten-1-ol, wherein said host cell prior to genetic modification does not produce 3-methyl-2-buten-1-ol, 3-methyl-3-buten-1-ol and 3-methyl-butan-1-ol.

21. The genetically modified host cell of claim 20, further comprising a second nucleic acid construct encoding a second enzyme capable of reducing a 3-methyl-2-buten-1-ol, wherein the first nucleic acid construct and the second nucleic acid construct reside on the same nucleic acid or two separate nucleic acids.

* * * * *